US008846984B2

(12) United States Patent
Allgeier et al.

(10) Patent No.: US 8,846,984 B2
(45) Date of Patent: Sep. 30, 2014

(54) PRODUCTION OF α,ω-DIOLS

(71) Applicant: E I du Pont de Nemours and Company, Wilmington, DE (US)

(72) Inventors: Alan Martin Allgeier, Wilmington, DE (US); Wathudura Indika Namal De Silva, Rahway, NJ (US); Carl Menning, Newark, DE (US); Joseph E Murphy, Woodbury, NJ (US); Joachim C Ritter, Wilmington, DE (US); Sourav Kumar Sengupta, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/870,072

(22) Filed: Apr. 25, 2013

(65) Prior Publication Data
US 2013/0289311 A1  Oct. 31, 2013

Related U.S. Application Data

(60) Provisional application No. 61/639,436, filed on Apr. 27, 2012.

(51) Int. Cl.
| C07C 27/04 | (2006.01) |
| C07C 29/132 | (2006.01) |
| C07C 209/16 | (2006.01) |
| C07D 309/06 | (2006.01) |
| C07C 29/60 | (2006.01) |
| B01J 27/188 | (2006.01) |
| B01J 23/888 | (2006.01) |

(52) U.S. Cl.
CPC ............ C07C 29/60 (2013.01); B01J 27/188 (2013.01); B01J 23/888 (2013.01); C07C 209/16 (2013.01)
USPC ............ 568/861; 564/479; 564/480; 549/427

(58) Field of Classification Search
USPC .......................................... 568/861; 549/427
See application file for complete search history.

(56) References Cited

U.S. PATENT DOCUMENTS

| 2,082,025 A | 6/1937 | Peters |
| 2,201,347 A | 5/1940 | Rittmeister |
| 2,440,929 A | 5/1948 | Frederick |
| 2,768,213 A | 10/1956 | Whetstone et al. |
| 3,070,633 A | 12/1962 | Utne et al. |
| 3,083,236 A | 3/1963 | Utne et al. |
| 3,189,651 A | 6/1965 | Ellery et al. |
| 3,215,742 A | 11/1965 | Horlenko et al. |
| 3,223,714 A | 12/1965 | Manly et al. |
| 3,268,588 A | 8/1966 | Horlenko et al. |
| 3,270,059 A | 8/1966 | Winderl |
| 3,917,707 A | 11/1975 | Williams et al. |
| 3,933,930 A | 1/1976 | Dougherty et al. |
| 4,254,059 A | 3/1981 | Grey |
| 4,400,468 A | 8/1983 | Faber |
| 4,401,823 A | 8/1983 | Arena |
| 4,780,552 A | 10/1988 | Wambach et al. |
| 5,112,994 A | 5/1992 | Koseki et al. |
| 5,210,335 A | 5/1993 | Schuster et al. |
| 5,412,111 A | 5/1995 | Matsumoto et al. |
| 5,538,891 A | 7/1996 | Schneider et al. |
| 5,696,303 A | 12/1997 | Darsow et al. |
| 5,981,769 A | 11/1999 | Baur et al. |
| 6,008,418 A | 12/1999 | Baur et al. |
| 6,087,296 A | 7/2000 | Harper et al. |
| 6,147,208 A | 11/2000 | Achhammer et al. |
| 6,265,602 B1 | 7/2001 | Voit et al. |
| 6,403,845 B1 | 6/2002 | Pfeffinger et al. |
| 6,407,294 B1 | 6/2002 | Breitscheidel et al. |
| 6,433,192 B1 | 8/2002 | Fischer et al. |
| 6,462,220 B1 | 10/2002 | Luyken et al. |
| 6,593,481 B1 | 7/2003 | Manzer |
| 6,818,781 B2 | 11/2004 | Bhatia |
| 7,019,155 B2 | 3/2006 | Manzer |
| 7,230,145 B2 * | 6/2007 | Kadowaki et al. ............ 568/865 |
| 8,053,608 B2 * | 11/2011 | Kouno et al. ................. 568/861 |
| 8,053,615 B2 | 11/2011 | Cortright et al. |
| 8,501,989 B2 | 8/2013 | Boussie et al. |
| 8,524,925 B2 | 9/2013 | Sabesan et al. |

(Continued)

FOREIGN PATENT DOCUMENTS

| CA | 2800797 A1 | 12/2011 |
| CN | 101628875 A | 1/2010 |

(Continued)

OTHER PUBLICATIONS

Co-pending U.S. Appl. No. 14/031,356, filed Sep. 19, 2013.
Co-pending U.S. Appl. No. 61/782,172, filed Mar. 14, 2013.
Co-pending U.S. Appl. No. 61/782,198, filed Mar. 14, 2013.
Notice of allowance dated Jan. 13, 2014 for copending U.S. Appl. No. 13/729,494.
International Search Report dated Mar. 29, 2013, PCT/US2012/062314.
International Search Report dated Apr. 29, 2013, PCT/US2012/071891.
International Search Report dated Apr. 29, 2013, PCT/US2012/071907.
International Search Report dated Apr. 29, 2013, PCT/US2012/071893.
International Search Report dated Apr. 29, 2013, PCT/US2012/071912.
International Search Report dated Apr. 30, 2013, PCT/US2012/071894.

(Continued)

Primary Examiner — Brian J Davis

(57) ABSTRACT

Disclosed herein are processes for preparing an α,ω-$C_n$-diol, wherein n is 5 or greater, from a feedstock comprising a $C_n$ oxygenate. In one embodiment, the process comprises contacting the feedstock with hydrogen gas in the presence of a catalyst comprising Cu, a Cu oxide, or mixtures thereof; a heteropoly acid component comprising $H_3[P(W_3O_{10})_4]$, $H_4[Si(W_3O_{10})_4]$, $H_4[P(Mo_3O_{10})_4]$, $H_4[Si(Mo_3O_{10})_4]$, $Cs_{2.5}H_{0.5}[P(W_3O_{10})_4]$, $Cs_{2.5}H_{0.5}[Si(W_3O_{10})_4]$, or mixtures thereof; optionally a second metal component comprising Cr, a Cr oxide, Ni, a Ni oxide, Mn, a Mn oxide, Fe, an Fe oxide, Co, a Co oxide, Mo, a Mo oxide, W, a W oxide, Re, a Re oxide, Zn, or a Zn oxide, Ag, a Ag oxide, $SiO_2$, or $Al_2O_3$; optionally at least one promoter comprising Na, K, Mg, Rb, Cs, Ca, Sr, Ba, Ce, or mixtures thereof; and optionally a support.

14 Claims, No Drawings

(56) References Cited

U.S. PATENT DOCUMENTS

| | | | |
|---|---|---|---|
| 8,669,393 | B2 | 3/2014 | Boussie et al. |
| 2003/0212298 | A1 | 11/2003 | Brasse et al. |
| 2006/0014988 | A1 | 1/2006 | Fischer et al. |
| 2007/0287845 | A1 | 12/2007 | Lilga et al. |
| 2008/0200698 | A1 | 8/2008 | Reichert et al. |
| 2009/0156841 | A1 | 6/2009 | Sanborn et al. |
| 2009/0314992 | A1 | 12/2009 | Pinkos et al. |
| 2010/0113841 | A1 | 5/2010 | Suzuki et al. |
| 2010/0216958 | A1 | 8/2010 | Peters et al. |
| 2010/0274030 | A1 | 10/2010 | Bevinakatti et al. |
| 2010/0317822 | A1 | 12/2010 | Boussie et al. |
| 2011/0040131 | A1 | 2/2011 | Kouno et al. |
| 2011/0071306 | A1 | 3/2011 | Robinson |
| 2011/0218318 | A1 | 9/2011 | Boussie et al. |
| 2011/0263916 | A1 | 10/2011 | Bao et al. |
| 2011/0312051 | A1 | 12/2011 | Kalnes et al. |
| 2012/0010419 | A1 | 1/2012 | Pinkos et al. |
| 2012/0022298 | A1 | 1/2012 | Pinkos et al. |
| 2012/0035399 | A1 | 2/2012 | Abillard et al. |
| 2012/0059174 | A1 | 3/2012 | Abillard et al. |
| 2012/0116122 | A1 | 5/2012 | Feist et al. |
| 2012/0172579 | A1 | 7/2012 | Qiao et al. |
| 2013/0172578 | A1 | 7/2013 | Allgeier et al. |
| 2013/0172586 | A1 | 7/2013 | Desilva et al. |
| 2013/0184495 | A1 | 7/2013 | Dias et al. |

FOREIGN PATENT DOCUMENTS

| | | | |
|---|---|---|---|
| CN | 102190639 | A | 9/2011 |
| DE | 4238493 | C1 | 4/1994 |
| EP | 110089 | B1 | 1/1988 |
| EP | 0411403 | A1 | 2/1991 |
| EP | 0418925 | A2 | 3/1991 |
| EP | 1243573 | A1 | 9/2002 |
| EP | 1243673 | A1 | 9/2002 |
| EP | 2390247 | A1 | 11/2011 |
| JP | 04041449 | A | 2/1992 |
| JP | 04046133 | A | 2/1992 |
| JP | 2003183200 | A | 7/2003 |
| JP | 2006036653 | A | 2/2006 |
| JP | 04555475 | B2 | 9/2010 |
| KR | 100645668 | B1 | 11/2006 |
| KR | 100688765 | B1 | 2/2007 |
| WO | 9955654 | A1 | 11/1999 |
| WO | 2007103586 | A2 | 9/2007 |
| WO | 2007103586 | A3 | 9/2007 |
| WO | 2009126852 | A1 | 10/2009 |
| WO | 2009133787 | A1 | 11/2009 |
| WO | 2010033789 | A2 | 3/2010 |
| WO | 2010033789 | A3 | 3/2010 |
| WO | 2010062689 | A2 | 6/2010 |
| WO | 2010099201 | A1 | 9/2010 |
| WO | 2010115759 | A2 | 10/2010 |
| WO | 2010115759 | A3 | 10/2010 |
| WO | 2010144873 | A1 | 12/2010 |
| WO | 2011149339 | A1 | 12/2011 |
| WO | 2013027766 | A1 | 2/2013 |
| WO | 2013066776 | A1 | 5/2013 |
| WO | 2013109477 | A1 | 7/2013 |

OTHER PUBLICATIONS

International Search Report dated Jul. 26, 2013, PCT/US2013/038403.
International Search Report dated Jul. 18, 2013, PCT/US2013/038418.
International Search Report dated Jul. 24, 2013, PCT/US2013/038441.
International Search Report dated Jul. 24, 2013, PCT/US2013/038436.
Office actions dated Jun. 26, 2013 and Sep. 13, 2013 for copending U.S. Appl. No. 13/729,390.
Office actions dated Sep. 27, 2013 and Dec. 17, 2013 for copending U.S. Appl. No. 13/729,464.
Notice of allowance dated Oct. 1, 2013 for copending U.S. Appl. No. 13/729,494.
Notice of allowance dated Nov. 19, 2013 for copending U.S. Appl. No. 13/729,401.
Office action dated Dec. 20, 2013 for copending U.S. Appl. No. 13/729,507.
Abe, R. et al, "Photocatalytic overall water splitting under visible light by TaON and WO3 with an IO3-/I-shuttle redox mediator", Chem Commun, 2005, 3829-3831.
Adkins, H. et al., "The catalytic hydrogenation of organic compounds over copper chromite", J Am Chem Soc (1931), vol. 53, 1093.
Alexeev, O.S. et al, "gamma-Al2O3-Supported Pt catalysts with extremely high dispersions resulting from Pt—W interactions", J Catal , 190 (2000) 157-17.
Binder et al., "Simple chemical transformation of lignocellulosic biomass into furans for fuels and chemicals", J Am Chem Soc (2009) 131, 1979-1985.
Blanc, B. et al, "Starch-derived polyols for polymer technologies: preparation by hydrogenolysis on metal catalysts", Green Chemistry, Apr. 2000, 89-91.
Buntara, T. et al, "Caprolactam from Renewable Resources: Catalytic Conversion of 5-Hydroxymethylfurfural into Caprolactone", Angew. Chem. Int. Ed. (2011), 50(31), 7083-7087.
Buntara, T. et al., "From 5-hydroxymethylfurfural (HMF) to polymer precursors: catalyst screening studies on the conversion of 1,2,6-hexanetriol to 1,6-hexanediol", Top Catal (2012) 55, 612-619.
Caes et al., "Conversion of Fructose into 5-(Hydroxymethyl)furfural in Sulfolane", ChemSusChem, (2011), 4(3), 353-356.
Chen, K. et al, "Chemoselective hydrogenolysis of tetrahydropyran-2-methanol to 1,6-hexanediol over rhenium-modified carbon-supported rhodium catalysts", ChemCatChem (2010) 2, 547-555.
Chen, K. et al, "C—O bond hydrogenolysis of cyclic ethers with OH groups over rhenium-modified supported iridium catalysts", J Catalysis (2012) vol. 294, 171-183.
Chia, M. et al, "Selective hydrogenolysis of polyols and cyclic ethers over bifunctional surface sites on rhodium—rhenium catalysts", J Am Chem Soc (2011) vol. 133, No. 32, 12675-12680.
Connor, R. et al, "Hydrogenolysis of Oxygenated Organic Compounds", J Am Chem Soc (1932), vol. 54, 4678-4690.
Corma, A. "Inorganic Solid Acids and Their Use in Acid-Catalyzed Hydrocarbon Reactions", (1995) Chem. Rev., 95, 559-614.
Diebold, U. "The surface science of titanium dioxide", Surface Science Reports 48 (2003) 53-229.
Efremov, A.A., "Transformations of levoglucosenone at the anhydroglucoside bond", Chem Natural Compounds (1998) 34, 5, 582-589.
Efremov, A.A. et al, "New thermocatalytic methods of chemicals producing from lignocellulosic materials in the presence of acid-type catalysts", Intl Symposium Wood Pulping Chemistry, 8th, Helsinki (1995) 689-696.
French, G.J. et al, "A re-investigation of the thermal decomposition of ammonium paratungstate", J. Mat. Sci, 16 (1981) 3427-3436.
Gong, L. et al, "Selective hydrogenolysis of glycerol to 1,3-propanediol over a Pt/WO3/TiO2/SiO2 catalyst in aqueous media", Appl Catal A General 390 (2010) 119-126.
Gong, X.Q. et al, "Small Au and Pt Clusters at the Anatase TiO2(101) Surface: Behavior at Terraces, Steps, and Surface Oxygen Vacancies", J. Am. Chem. Soc. 130 (2008) 370-381.
Helberger et al, Justus Liebigs Annalen der Chemie (1949) 561, 215-220.
Huang, L. et al, "Direct conversion of glycerol into 1,3-propanediol over Cu—H4SiW12O40/SiO2 in vapor phase", Catal Lett, 131 (2009) 312-320.
Jae, J. et al, "Investigation into the shape selectivity of zeolite catalysts for biomass conversion", Journal of Catalysis (2011) 279, 257-268.
Jalil, P.A. et al, "A Study of Stability of Tungstophosphoric Acid, H3PW12O40, Using Synchrotron XPS, XANES, Hexane Cracking, XRD and IR Spectroscopy", J. Catalysis, 2003, 217(2), 292-297.
Jayaraman, S. et al, "Synthesis and Characterization of Pt—WO3 as Methanol Oxidation Catalysts for Fuel Cells", J Phys Chem B, 2005, 109, 22958-22966.

(56) References Cited

OTHER PUBLICATIONS

Jung, M.E. et al, "Synthesis of Methylene-Expanded 2',3'-Dideoxyribonucleosides", J Organic Chemistry 63 (1998) 8133-8144.
Kamalakar, G. et al, "tert-Butylation of Phenol over Ordered Solid Acid Catalysts in Supercritical Carbon Dioxide: Efficient Synthesis of 2,4-Di-tert-butylphenol and 2,4,6-Tri-tert-butylphenol", Ind Eng Chem Res, 45 (2006) 6118-6126.
Karinen, R. et al, "Biorefining: heterogeneously catalyzed reactions of carbohydrates for the production of furfural and hydroxymethyfurfural", Chem Sus Chem (2011) 4, 1002-1016.
Kaufmann, W.E. et al, "The use of platinum oxide as a catalyst in the reduction of organic compounds. IV. Reduction of furfural and its derivatives", J Am Chem Soc (1923) 45, 3029-3044.
Kiss, A.B. et al, "Thermal polycondensation of ammonium paratungstate, $(NH_4)_{10}[W_{12}O_{40}(OH)_2] \cdot 4H_2O$", J. Materials Sci, 13 (1978) 2541-2547.
Koso, S. et al, "Chemoselective hydrogenolysis of tetrahydrofurfuryl alcohol to 1,5-pentanediol", Chem. Commun. (2009) 2035-2037.
Koso, S. et al, "Promoting effect of Mo on the hydrogenolysis of tetrahydrofurfuryl alcohol to 1,5-pentanediol over $Rh/SiO_2$", J Catalysis 267 (2009), 89-92.
Kuba, S. et al, "Structure and properties of tungstated zirconia catalysts for alkane conversion", J Catalysis, 216 (2003) 353-361.
Lee, U. et al, "Structure of pentasodium trihydrogenhexatungstoplatinate(IV) icosahydrate", Acta Cryst. (1983) C39, 817-819.
Li, N.; Huber, G.W., "Aqueous-phase hydrodeoxygenation of sorbitol with $Pt/SiO_2$—$Al_2O_3$: identification of reaction intermediates", Journal of Catalysis (2010) 270, 48-59.
Li, N. et al, "Renewable gasoline from aqueous phase hydrodeoxygenation of aqueous sugar solutions prepared by hydrolysis of maple wood", Green Chemistry 2011, 13, 91-101.
Liu, L. et al, "Mesoporous $WO_3$ supported Pt catalyst for hydrogenolysis of glycerol to 1,3-propanediol", Chin. J Catal., 2012, 33, 1257-1261.
Miftakhov, M.S. et al, "Levoglucosenone: the properties, reactions, and use in fine organic synthesis", Russian Chem Reviews (1994) 63(10) 869-882.
Nakagawa, Y. et al, "Heterogeneous catalysis of the glycerol hydrogenolysis", Catal Sci Technol 2011, 1, 179-190.
Nakagawa, Y. et al., "Production of 1,5-pentanediol from biomass via furfural and tetrahydrofurfuryl alcohol", Catalysis Today 195 (2012) 136-143.
Nikolla, E. et al., "'One-Pot' Synthesis of 5-(Hydroxymethyl)furfural from Carbohydrates Using Tin-Beta Zeolite", ACS Catal. (2011), 1, 408-410.
Okuhara, T. et al, "Insoluble heteropoly compounds as highly active catalysts for liquid-phase reactions", J. Mol. Catal. 74 (1992) 247-256.
Ott, L. et al, "Catalytic Dehydration of Glycerol in sub- and supercritical water: a new chemical process for acrolein production", Green Chemistry, 2006, pp. 214-220, vol. 8.
Pae, Y.I. et al, "Characterization of $NiO-TiO_2$ modified with $WO_3$ and catalytic activity for acid catalysis", Bull. Korean Chem. Soc. 2004, vol. 25(12), 1881-1888.
Ponder, G. R. et al, "Pyrolytic Conversion of Biomass of Anhydrosugars—Influences of Indigenous Ions and Polysaccharide Structures", Applied Biochem Biotech, 1990, vol. 24/25, p. 41-47.
Roman-Leshkov, Y. et al., "Solvent effects on fructose dehydration to 5-hydroxymethylfurfural in biphasic systems saturated with inorganic salts", Top Catal (2009) 52:297-303.
Shafizadeh, F. et al., "Some Reactions of Levoglucosenone", Carbohydrate Research, 1979, pp. 169-191, vol. 71.
SRI Process Economics Program, 31, Hexamethylenediamine Nov. 1967.
Ten Dam, J. et al, "$Pt/Al_2O_3$ catalyzed 1,3-propanediol formation from glycerol using tungsten additives", ChemCatChem (2013), 5(2), 497-505.
Tong, X. et al, "Biomass into chemicals: conversion of sugars to furan derivatives by catalytic processes", Appl. Catalysis A General, 385 (2010) 1-13.
Tripathy, P.K. et al, "A comparative study on the thermal decomposition of ammonium p—tungstate in batch and fluidized-bed reactors", Ind Eng Chem Res 36 (1997) 3602-3606.
Trost, B. M. "Cyclizations Made Easy by Transition Metal Catalysts", in Homogeneous Transition Metal Catalyzed Reactions; Moser, W. et al; Adv. Chem. 31, 1992, ACS, Washington, DC.
Xu, W. et al, "Direct catalytic conversion of furfural to 1,5-pentanediol by hydrogenolysis of the furan ring under mild conditions over $Pt/Co_2AlO_4$ catalyst" Chem Comm, Royal Society of Chemistry (2011) vol. 47, No. 13, 3924-3926.
Yamazoe, S. et al, "XAFS Study of Tungsten L1-, L3-Edges: Structural Analysis of Loaded Tungsten Oxide Species", Envir Sci, Research Frontiers 2008, Spring 8, 138-139.
Yamazoe, S. et al, "XAFS Study of Tungsten L1- and L3-Edges: Structural Analysis of $WO_3$ Species Loaded on $TiO_2$ as a Catalyst for Photo-oxidation of $NH_3$", J. Phys Chem C 2008, 112, 6869-6879.
Yoshinaga, Y. et al, "Shape-selective oxidation catalysed by a Pt-promoted ultramicroporous heteropoly compound", J.Chem. Soc. Faraday Trans 1998, 94(15) 2235-2240.
Zanardi, M.M. et al, "Synthesis of a simple chiral auxiliary derived from levoglucosenone and its application in a Diels-Alder reaction", Tetrahedron letters 50 (2009) 999-1002.
Office action dated Feb. 27, 2014 for copending U.S. Appl. No. 13/870,095.
Office action dated Feb. 27, 2014 for copending U.S. Appl. No. 13/870,099.
Alamillo, R. et al., "Selective Hydrogenation of Biomass-Derived 5-Hydroxymethylfurfural Using Heterogeneous Catalysts", Green Chem., 2012, 14, 1413.
Jung, K.J. et al., "Furfural Decarbonylation Catalyzed by Charcoal Supported Palladium: Part I—Kinetics", Biomass 16 (1988) 63-76.
Jung, K.J. et al., "Furfural Decarbonylation Catalyzed by Charcoal Supported Palladium: Part II—A Continuous Process", Biomass 16 (1988) 89-96.
Lichtenthaler, F.W. "Carbohydrates as Organic Raw Materials" 2010 Wiley-VCH Verlag GmbH&Co. KGaA, Weinheim 10.1002/14356007.n05_n07.
Qin, L.-Z. et al., "Aqueous-phase deoxygenation of glycerol to 1,3-propanediol over $Pt/WO_3/ZrO_2$ catalysts in a fixed-bed reactor", Green Chem., 2010, 12, 1466-1472.
Rao, R.S. et al., "Furfural Hydrogenation Over Carbon-Supported Copper", Catalysis Letters 60 (1999) 51-57.
Zheng, H.-Y. et al., "Towards Understanding the Reaction Pathway in Vapour Phase Hydrogenation of Furfural to 2-Methylfuran", J Molecular Catalysis A: Chemical 246 (2006) 18-23.
Efremov, A.A. et al, "Conversions of Levoglucosenone in Acid Media", Sibirskii Khimicheskii Zhurnal 1992, 6, 34-39 Translation.
Co-pending application published as US-2013-0172579-A1, Filed Dec. 28, 2012.
Co-pending application published as 2013-0172586-A1, Filed Dec. 28, 2012.
Co-pending application published as US-2013-0172578-A1, Filed Dec. 28, 2012.
Co-pending application published as US-2013-0172629-A1, Filed Dec. 28, 2012.
Co-pending application published as US-2013-0172580-A1, Filed Dec. 28, 2012.
Co-pending application published as US-2013-0289319-A1, Filed Apr. 25, 2013.
Co-pending application published as US-2013-0289312-A1, Filed Apr. 25, 2013.
Co-pending application published as US-2013-0289318-A1, Filed Apr. 25, 2013.
Co-pending application U.S. Appl. No. 13/870,095, filed Apr. 25, 2013.
Co-pending application published as US-2013-0231505-A1, Filed Apr. 25, 2013.
International Search Report dated May 6, 2014, PCT/US2012/062314.

(56) References Cited

OTHER PUBLICATIONS

Copending application No. PCT/US14/23874 filed Mar. 12, 2014.
Copending application No. PCT/US14/23905 filed Mar. 12, 2014.
Office action dated Apr. 9, 2014 for copending U.S. Appl. No. 13/870,080.
Notice of allowance dated Apr. 25, 2014 for copending U.S. Appl. No. 13/729,464.
Notice of allowance dated Apr. 28, 2014 for copending U.S. Appl. No. 13/729,494.
Notice of allowance dated Apr. 29, 2014 for copending U.S. Appl. No. 13/729,507.
Office action dated May 7, 2014 for copending U.S. Appl. No. 13/729,390.
Database CAPLUS on STN, AN 1979:151575, Nishino et al, JP 53149905 A, Dec. 27, 1978.
Database WPIX on STN, AN 1979-11181B [197906], Nishino et al, JP53149905 a Dec. 27, 1978 (abstract).
notice of allowance dated Mar. 11, 2014 for copending U.S. Appl. No. 13/870,091.

* cited by examiner

US 8,846,984 B2

PRODUCTION OF α,ω-DIOLS

This application claims priority under 35 U.S.C. §119(e) from, and claims the benefit of, U.S. Provisional Application No. 61/639,436 filed Apr. 27, 2012, which is by this reference incorporated in their entirety as a part hereof for all purposes.

FIELD OF DISCLOSURE

The present invention relates to processes for preparing alpha, omega-diols ("α,ω-diols"). More particularly, the present invention relates to processes for preparing α,ω-diols by selective hydrodeoxygenation of oxygenated compounds which can be derived from carbohydrates or biologic sources.

BACKGROUND

Alpha, omega-diols such as 1,5-pentanediol and 1,6-hexanediol are useful as chemical intermediates for the production of, e.g., agrichemicals, pharmaceuticals, and polymers. For example, α,ω-diols can be used as plasticizers and as comonomers in polyesters and polyether-urethanes. It has become increasingly desirable to obtain industrial chemicals such as α,ω-diols, or their precursors, from materials that are not only inexpensive but also benign in the environment. Of particular interest are materials which can be obtained from renewable sources, that is, materials that are produced by a biological activity such as planting, farming, or harvesting. As used herein, the terms "renewable" and "biosourced" can be used interchangeably.

Biomass sources for such materials are becoming more attractive economically versus petroleum-based ones. Although the convergent and selective synthesis of $C_5$ and $C_6$ carbocyclic intermediates from biomass is difficult because of the high degree of oxygenation of many components of biomass, use of such biomass-derived intermediates as feedstocks would offer new routes to industrially useful chemicals.

1,6-Hexanediol is a useful intermediate in the industrial preparation of nylon 66. 1,6-Hexanediol can be converted by known methods to 1,6-hexamethylene diamine, a starting component in nylon production. 1,6-Hexanediol is typically prepared from the hydrogenation of adipic acid or its esters or the hydrogenation of caprolactone or its oligomers. For example, in WO 2011/149339, deVries J-G, et al describe a process for the preparation of caprolactone, caprolactam, 2,5-tetrahydrofuran-dimethanol, 1,6-hexanediol or 1,2,6-hexanetriol from 5-hydroxymethyl-2-furfuraldehyde and teach that 1,2,6-hexanetriol may be hydrogenated to 1,6-hexanediol using a catalyst based on palladium, nickel, rhodium, ruthenium, copper and chromium or mixtures thereof. Further, the catalysts may be doped with one or more other elements, such as rhenium.

JP 2003-183200 teaches a method for preparation of 2,5-diethyl-1,6-hexanediol from tetrahydropyran derivatives, e.g. 2,5-dimethyltetrahydropyran-2-methanol, comprising hydrogenation of the starting material in the presence of a metal catalyst carried on an acidic support, notably 5% $Pt/Al_2O_3$ and 5% $Pt/SiO_2$—$Al_2O_3$ at 200-240° C. Yields ranged from 40 to 61%.

There is an existing need for processes to make α,ω-diols, especially $O_5$ and $O_6$ α,ω-diols, and synthetic intermediates useful in the production of α,ω-diols, from renewable biosources. There is an existing need for processes to produce 1,5-pentanediol, 1,6-hexanediol, and other α,ω-diols at high yield and high selectivity from biomass-derived starting materials, including 1,2,6-hexanetriol, tetrahydrofuran-2,5-dimethanol, and 2-hydroxymethyltetrahydropyran.

SUMMARY

In one embodiment, a process is provided for preparing an α,ω-$C_n$-diol is provided, the process comprising the steps:
(a) providing a feedstock comprising a $C_n$ oxygenate;
(b) contacting the feedstock with hydrogen gas, in the presence of a catalyst and at a temperature and for a time sufficient to form a product mixture comprising an α,ω-$C_n$-diol;
wherein n is 5 or greater; and wherein the catalyst comprises a first metal component, a heteropoly acid component, optionally a second metal component, optionally at least one promoter, and optionally a support; wherein:
the first metal component comprises Cu, a Cu oxide, or mixtures thereof;
the heteropoly acid component comprises $H_3[P(W_3O_{10})_4]$, $H_4[Si(W_3O_{10})_4]$, $H_4[P(Mo_3O_{10})_4]$, $H_4[Si(Mo_3O_{10})_4]$, $Cs_{2.5}H_{0.5}[P(W_3O_{10})_4]$, $Cs_{2.5}H_{0.5}[Si(W_3O_{10})_4]$, or mixtures thereof;
the second metal component comprises Cr, a Cr oxide, Ni, a Ni oxide, Mn, a Mn oxide, Fe, an Fe oxide, Co, a Co oxide, Mo, a Mo oxide, W, a W oxide, Re, a Re oxide, Zn, or a Zn oxide, Ag, a Ag oxide, $SiO_2$, or $Al_2O_3$; and
the promoter comprises Na, K, Mg, Rb, Cs, Ca, Sr, Ba, Ce, or mixtures thereof.

In one embodiment, the optional second metal component is present in the catalyst and comprises Cr, a Cr oxide, Mn, a Mn oxide, Zn, a Zn oxide, or mixtures thereof.

In one embodiment, the optional support is present in the catalyst and comprises $WO_3$, $SiO_2$, $Al_2O_3$, carbon, $TiO_2$, $ZrO_2$, $SiO_2$—$Al_2O_3$, montmorillonite, $SiO_2$—$TiO_2$, tungstated $ZrO_2$, zeolites, $V_2O_5$, $MoO_3$, or mixtures thereof. In one embodiment, the solid support comprises $SiO_2$.

In one embodiment, the $C_n$ oxygenate comprises 1,2,6-hexanetriol; 1,2,5-pentanetriol; 2H-tetrahydropyran-2-methanol; tetrahydrofuran-2,5-dimethanol; furan-2,5-dimethanol; 2,5 dihydrofuran-2,5-dimethanol; levoglucosenone; levoglucosan; isosorbide; hydroxymethyl-furfural; sorbitol; glucose; fructose; xylitol; 3,4-dihydro-2H-pyran-2-carbaldehyde; 1,2,5,6-hexanetetraol; 1,2,3,5,6-hexanepentanol; 1,5-anhydro-3,4-dideoxy-hexitol; 5-hydroxy-2H-tetrahydropyran-2 methanol; furfural; furfuryl alcohol; tetrahydrofurfuryl alcohol; pentoses; dimers containing pentose; oligomers containing pentose; hexoses; dimers containing hexose; oligomers containing hexose; condensation products from the reaction of 5-(hydroxymethyl)-2-furfural with ketones and/or aldehydes; and condensation products from the reaction of furfural with ketones and/or aldehydes.

DETAILED DESCRIPTION

As used herein, where the indefinite article "a" or "an" is used with respect to a statement or description of the presence of a step in a process of this invention, it is to be understood, unless the statement or description explicitly provides to the contrary, that the use of such indefinite article does not limit the presence of the step in the process to one in number.

As used herein, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

As used herein, the term "about" modifying the quantity of an ingredient or reactant employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. The term "about" may mean within 10% of the reported numerical value, preferably within 5% of the reported numerical value.

As used herein, the term "organic compound" means a carbon-containing compound with the following exceptions: binary compounds as the carbon oxides, carbides, carbon disulfide, etc.; ternary compounds such as metallic cyanides, metallic carbonyls, phosgene, carbonylsulfide; and metallic carbonates such as calcium carbonate and sodium carbonate.

As used herein, the term "oxygenate" means an organic compound containing at least one oxygen atom. As used herein, the term "$C_r$, oxygenate" means an oxygenate containing n carbon atoms and, analogously, the term "$C_r$, diol" denotes a diol containing n carbon atoms.

As used herein, the term "biomass" refers to any cellulosic or lignocellulosic material and includes materials comprising hemicellulose, and optionally further comprising lignin, starch, oligosaccharides and/or monosaccharides.

As used herein, the term "lignocellulosic" means comprising both lignin and cellulose. Lignocellulosic material may also comprise hemicellulose. In some embodiments, lignocellulosic material contains glucan and xylan.

As used herein, the term "hemicellulose" means a non-cellulosic polysaccharide found in lignocellulosic biomass. Hemicellulose is a branched heteropolymer consisting of different sugar monomers. It typically comprises from 500 to 3000 sugar monomeric units.

As used herein, the term "lignin" refers to a complex high molecular weight polymer that can comprise guaiacyl units, as in softwood lignin, or a mixture of guaiacyl and syringyl units, as in hardwood lignin.

As uses herein, the term "starch" refers to a carbohydrate consisting of a large number of glucose units joined by glycosidic bonds. Starch, also known as amylum, typically contains amylose and amylopectin.

As used herein, the term "sugar" includes monosaccharides, disaccharides, and oligosaccharides. Monosaccharides, or "simple sugars," are aldehyde or ketone derivatives of straight-chain polyhydroxy alcohols containing at least three carbon atoms. A pentose is a monosaccharide having five carbon atoms; examples include xylose, arabinose, lyxose, and ribose. A hexose is a monosaccharide having six carbon atoms; examples include glucose and fructose. Disaccharide molecules consist of two covalently linked monosaccharide units; examples include sucrose, lactose, and maltose. As used herein, "oligosaccharide" molecules consist of about 3 to about 20 covalently linked monosaccharide units. Unless indicated otherwise herein, all references to specific sugars are intended to include the D-stereoisomer, the L-stereoisomer, and mixtures of the stereoisomers.

As used herein, the term "$C_r$ sugar" includes monosaccharides having n carbon atoms; disaccharides comprising monosaccharide units having n carbon atoms; and oligosaccharides comprising monosaccharide units having n carbon atoms. Thus, the term "$C_5$ sugar" includes pentoses, disaccharides comprising pentose units, and oligosaccharides comprising pentose units; the term "$O_6$ sugar" includes hexoses, disaccharides comprising hexose units, and oligosaccharides comprising hexose units.

As used herein, the term "$C_r$ sugar alcohol" refers to compounds produced from $C_r$ sugars by reduction of the carbonyl group to a primary or secondary hydroxyl group. Sugar alcohols having the general formula $H(HCHO)_{x+1}H$, are derived from sugars having the general formula $H(HCHO)_xHCO$. Monosaccharides and disaccharides can be used to form sugar alcohols, though the disaccharides are not fully hydrogenated. Three examples of sugar alcohols are xylitol ($C_5$), sorbitol ($C_6$), and mannitol ($C_6$).

As used herein, the abbreviation "16HD" refers to 1,6-hexanediol. The chemical structure of 1,6-hexanediol is represented by Formula (I).

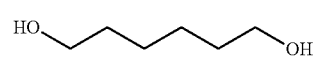

As used herein, the abbreviation "15PD" refers to 1,5-pentanediol. The chemical structure of 1,5-pentanediol is represented by Formula (II).

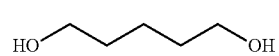

As used herein, the abbreviation "126HT" refers to 1,2,6-hexanetriol and includes a racemic mixture of isomers. The chemical structure of 1,2,6-hexanetriol is represented by Formula (III).

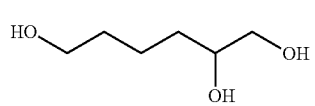

As used herein, the abbreviation "125PT" refers to 1,2,5-pentanetriol and includes a racemic mixture of isomers. The chemical structure of 1,2,5-pentanetriol is represented by Formula (IV).

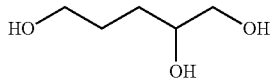

IV

As used herein, the abbreviation "Tetraol" refers to 1,2,5,6-tetrahydroxyhexane, also known as 3,4-dideoxyhexitol, and includes a mixture of stereoisomers. The chemical structure of 1,2,5,6-tetrahydroxyhexane is represented by Formula (V).

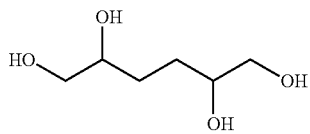

V

As used herein, the abbreviation "Pentaol" refers to 1,2,3,5,6-hexanepentaol and includes a racemic mixture of isomers. The chemical structure of 1,2,3,5,6-hexanepentaol is represented by Formula (VI).

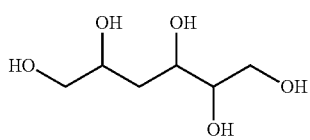

VI

As used herein, the abbreviation "THFdM" refers to tetrahydro-2,5-furandimethanol (also known as tetrahydrofuran-2,5-dimethanol or 2,5-tetrahydrofurandimethanol, or 2,5-bis[hydroxymethyl]tetrahydrofuran) and includes a mixture of stereoisomers (cis and racemic trans isomers). The chemical structure of tetrahydro-2,5-furandimethanol is represented by Formula (VII).

VII

The chemical structure of 2,5-dihydrofuran-2,5-dimethanol is represented by Formula (VIII).

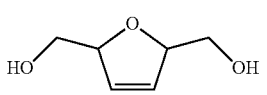

VIII

As used herein, the abbreviation "FdM" refers to 2,5-furandimethanol, also known as 2,5-bis(hydroxymethyl)furan. The chemical structure of 2,5-furandimethanol is represented by Formula (IX).

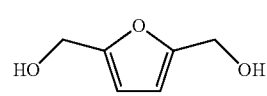

IX

The chemical structure of furfural, also known as furan-2-carbaldehyde or 2-furaldehyde, is represented by Formula (X).

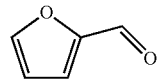

X

The chemical structure of hydroxymethylfurfural, also known as 5-(hydroxymethyl)-2-furaldehyde, is represented by Formula (XI).

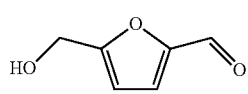

XI

The chemical structure of furfuryl alcohol, also known as 2-furanmethanol, is represented by Formula (XII).

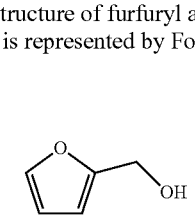

XII

The chemical structure of tetrahydrofurfuryl alcohol, also known as tetrahydro-2-furanmethanol, is represented by Formula (XIII).

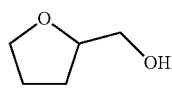

XIII

As used herein, the abbreviation "THPM" refers to tetrahydro-2H-pyran-2-methanol, also known as 2-hydroxymethyltetrahydropyran, and includes a racemic mixture of isomers. The chemical structure of tetrahydro-2H-pyran-2-methanol is represented by Formula (XIV).

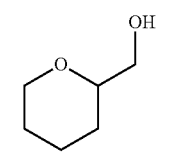

XIV

As used herein, the abbreviation "HOTHPM" refers to 2-hydroxymethyl-5-hydroxytetrahydro-2H-pyran, also known as 5-hydroxy-2H-tetrahydropyran-2 methanol or 1,5-anhydro-3,4-dideoxyhexitol, and includes a mixture of stereoisomers. The chemical structure of 2-hydroxymethyl-5-hydroxytetrahydro-2H-pyran is represented by Formula (XV).

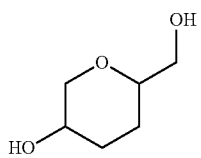

XV

The chemical structure of 3,4-dihydro-2H-pyran-2-carbaldehyde, also known as 3,4-dihydro-2H-pyran-2-carboxaldehyde, 2-formyl-3,4-dihydro-2H-pyran, or "acrolein dimer", is represented by Formula (XVI).

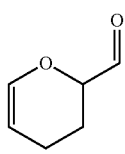

XVI

The chemical structure of levoglucosan, also known as 1,6-anhydro-β-glucopyranose, is represented by Formula (XVII).

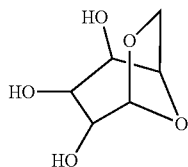

XVII

As used herein, the abbreviations "Lgone" and "LGone" refer to levoglucosenone, also known as 1,6-anhydro-3,4-dideoxy-β-D-pyranosen-2-one. The chemical structure of levoglucosenone is represented by Formula (XVIII).

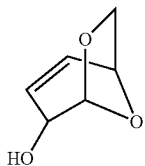

XVIII

The chemical structure of 1,6-anhydro-3,4-dideoxy-p-D-pyranose-2-one is represented by Formula (XIX).

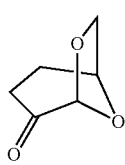

XIX

The chemical structure of levoglucosenol, also known as 1,6-anhydro-3,4-dideoxy-β-erythro-hex-3-enopyranose, is represented by Formula (XX).

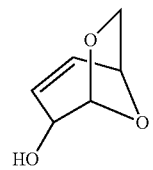

XX

As used herein, the abbreviations "Lgol" and "LGol" refer to levoglucosanol, also known as 1,6-anhydro-3,4-dideoxyhexopyranose, and include a mixture of the threo and erythro stereoisomers. The chemical structure of 1,6-anhydro-3,4-dideoxyhexopyranose is represented by Formula (XXI).

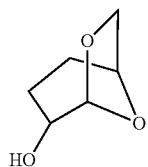

XXI

As used herein, the abbreviation "ISOS" refers to isosorbide, also known as 1,4:3,6-dianhydrosorbitol or 1,4-dianhydrosorbitol. The chemical structure of isosorbide is represented by Formula (XXII).

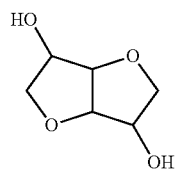

XXII

The chemical structure of sorbitol, also known as hexane-1,2,3,4,5,6-hexyl, is represented by Formula (XXIII).

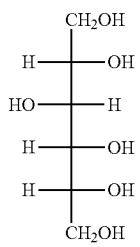

XXIII

The chemical structure of glucose, also known as dextrose or 2,3,4,5,6-pentahydroxyhexanal, is represented by Formula (XXIV).

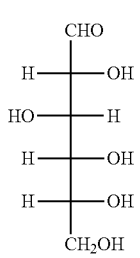

XXIV

The chemical structure of fructose, also known as levulose, is represented by Formula (XXV).

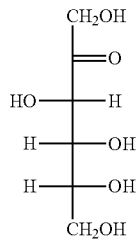

The chemical structure of xylitol, also known as pentane-1,2,3,4,5-pentol, is represented by Formula (XXVI).

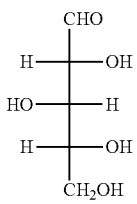

In one embodiment, a process is provided for preparing an $\alpha,\omega$—$C_n$-diol, the process comprising the steps:

(a) providing a feedstock comprising a $C_n$ oxygenate;

(b) contacting the feedstock with hydrogen gas, in the presence of a catalyst and at a temperature and for a time sufficient to form a product mixture comprising an $\alpha,\omega$—$C_n$-diol;

wherein n is 5 or greater; and wherein the catalyst comprises a first metal component, a heteropoly acid component, optionally a second metal component, optionally at least one promoter, and optionally a solid support; wherein the first metal component comprises Cu, a Cu oxide, or mixtures thereof;

the heteropoly acid component comprises $H_3[P(W_3O_{10})_4]$, $H_4[Si(W_3O_{10})_4]$, $H_4[P(Mo_3O_{10})_4]$, $H_4[Si(Mo_3O_{10})_4]$, $Cs_{2.5}H_{0.5}[P(W_3O_{10})_4]$, $Cs_{2.5}H_{0.5}[Si(W_3O_{10})_4]$, or mixtures thereof;

the second metal component comprises Cr, a Cr oxide, Ni, a Ni oxide, Mn, a Mn oxide, Fe, an Fe oxide, Co, a Co oxide, Mo, a Mo oxide, W, a W oxide, Re, a Re oxide, Zn, or a Zn oxide, Ag, a Ag oxide, $SiO_2$, or $Al_2O_3$; and the promoter comprises Na, K, Mg, Rb, Cs, Ca, Sr, Ba, Ce, or mixtures thereof.

In one embodiment, n=5 or 6. In one embodiment, n=5, and the $\alpha,\omega$-$C_n$-diol is 1,5-pentanediol. In one embodiment, n=6, and the $\alpha,\omega$-$C_n$-diol is 1,6-hexanediol. In one embodiment, n=7, and the $\alpha,\omega$-$C_n$-diol is 1,7-heptanediol. In one embodiment, n=8, and the $\alpha,\omega$-$C_n$-diol is 1,8-octanediol.

The first metal component comprises Cu, a Cu oxide, or mixtures thereof and can be present in the catalyst in an amount ranging from about 2 weight percent to about 50 weight percent, for example from about 5 weight percent to about 45 weight percent, or from about 5 weight percent to about 40 weight percent of the catalyst.

The heteropoly acid component comprises one or more heteropoly acids including, but not limited to, phosphotungstic acid $H_3[P(W_3O_{10})_4]$, silicotungstic acid $H_4[Si(W_3O_{10})_4]$, molybdophosphoric acid $H_4[P(Mo_3O_{10})_4]$, and silicomolybdic acid $H_4[Si(Mo_3O_{10})_4]$. The heteropoly acid component may include $H_4PW_{11}VO_{40}$. The heteropoly acid component can be used in the acid form (H+ cation), as a partially exchanged salt, or as a fully-exchanged salt. In one embodiment, the heteropoly acid component comprises partially cesium-exchanged, partially potassium-exchanged, partially rubidium-exchanged, or partially ammonium-exchanged salts of a heteropoly acid, or mixtures of two or more such salts. In one embodiment, the heteropoly acid component comprises one or more partially cesium-exchanged salts of a heteropoly acid, for example $Cs_{2.5}H_{0.5}[P(W_3O_{10})_4]$ or $Cs_{2.5}H_{0.5}[Si(W_3O_{10})_4]$. In one embodiment, the heteropoly acid component comprises $H_3[P(W_3O_{10})_4]$, $H_4[Si(W_3O_{10})_4]$, $H_4[P(Mo_3O_{10})_4]$, $H_4[Si(Mo_3O_{10})_4]$, $Cs_{2.5}H_{0.5}[P(W_3O_{10})_4]$, or $Cs_{2.5}H_{0.5}[Si(W_3O_{10})_4]$. In one embodiment, the heteropoly acid component comprises $H_3[P(W_3O_{10})_4]$, $H_4[Si(W_3O_{10})_4]$, or $Cs_{2.5}H_{0.5}[P(W_3O_{10})_4]$. The heteropoly acid component is present in the catalyst at a ratio of the first metal component to the heteropoly acid component in a range from about 9:1 to about 1:99 on a weight basis. In one embodiment, the ratio of the first metal component to the heteropoly acid component is about 1:1 on a weight basis.

Optionally, a second metal component is present in the catalyst and comprises Cr, a Cr oxide, Ni, a Ni oxide, Mn, a Mn oxide, Fe, an Fe oxide, Co, a Co oxide, Mo, a Mo oxide, W, a W oxide, Re, a Re oxide, Zn, or a Zn oxide, Ag, a Ag oxide, $SiO_2$, or $Al_2O_3$. In one embodiment, the optional second metal component is present in the catalyst and comprises Cr, a Cr oxide, Mn, a Mn oxide, Zn, a Zn oxide, or mixtures thereof.

In some embodiments, the catalyst comprises from 2 wt % to 98 wt % Cu and/or CuO as the first metal component, and further comprises from 98 wt % to 2 wt % of at least one oxide which comprises the second metal component and/or the promoter, wherein the weight percentages are based on the total weight of the first metal component, the second metal component where present, and the promoter where present. The at least one oxide is selected from the group consisting of zinc oxide (ZnO), magnesium oxide (MgO), barium oxide (BaO), chromium oxide ($Cr_2O_3$), silica ($SiO_2$), alumina ($Al_2O_3$), zirconium dioxide ($ZrO_2$), nickel oxide (NiO), manganese oxide ($MnO_2$), sodium oxide ($Na_2O$), potassium oxide ($K_2O$), cerium oxide ($CeO_2$), lanthanum oxide ($La_2O_3$), iron oxide ($Fe_2O_3$), silver oxide ($Ag_2O$) and cobalt oxide ($Co_2O_3$). In one embodiment, the second metal component comprises ZnO. In one embodiment, the promoter comprises MgO. In some embodiments, the catalyst further comprises carbon. Examples of suitable commercially available materials which comprise the first metal component and at least one oxide comprising the second metal component and/or the promoter include but are not limited to the following: CuO/ZnO, BaO/CuO/$Cr_2O_3$/$SiO_2$, BaO/CuO/$Cr_2O_3$, BaO/CuO/$MnO_2$/$Cr_2O_3$, CuO/$SiO_2$, CuO/$Al_2O_3$, CuO/NiO/$Al_2O_3$, CuO/$Cr_2O_3$/$MnO_2$, CuO/$Cr_2O_3$, CuO/$MnO_2$, CuO/$Cr_2O_3$, CuO/ZnO/$Al_2O_3$, CuO/$SiO_2$/$Cr_2O_3$/MgO, CuO/ZnO/$CeO_2$/$Al_2O_3$/$Na_2O$/C, CuO/NiO, and NiO/CuO/$K_2O$/$Cr_2O_3$/$CaF_2$. In one embodiment, materials which comprise the first metal component and at least one oxide comprising the second metal component and/or the promoter comprise CuO/ZnO, CuO/ZnO/$Al_2O_3$, or CuO/ZnO/$CeO_2$/$Al_2O_3$/$Na_2O$/C. In one embodiment, such material comprises CuO/ZnO/$Al_2O_3$.

Optionally, the catalyst comprises at least one promoter. The promoter comprises Na, K, Mg, Rb, Cs, Ca, Sr, Ba, Ce, or mixtures thereof. In one embodiment, the promoter comprises Ba, Cs, or mixtures thereof. In one embodiment, an oxide contains the promoter, such as described herein above.

The promoter is present in the catalyst in an amount ranging from 0 to about 20 weight percent, for example from about 0 to about 15, or from about 1 to about 10, or from about 1 to about 5, weight percent. In one embodiment, the heteropoly acid component further comprises the promoter. In one embodiment, the first metal component further comprises the promoter. In one embodiment, the catalyst comprises a second metal component, and the second metal component further comprises the promoter, for example as an oxide.

In some embodiments, it is useful to utilize a catalyst which comprises a solid support to enhance the stability and economic feasibility of the process. Examples of useful supports include $WO_3$, $SiO_2$, $Al_2O_3$, carbon, SiC, $TiO_2$, $ZrO_2$, $SiO_2$—$Al_2O_3$, clays such as montmorillonite, $SiO_2$—$TiO_2$, tungstated $ZrO_2$, $V_2O_5$, $MoO_3$, and zeolites such as H—Y, FAU (H—Y or USY), BEA (H-Beta), MFI (H—ZSM5), MEL (H—ZSM11) and MOR(H-Mordenite). Typically, tungstated $ZrO_2$ can comprise up to about 19 wt % W as $WO_3$ on $ZrO_2$, see for example S. Kuba et al in Journal of Catalysis 216 (2003), p. 353-361. In one embodiment, the catalyst further comprises a solid support comprising $WO_3$, $SiO_2$, $Al_2O_3$, carbon, $TiO_2$, $ZrO_2$, $SiO_2$—$Al_2O_3$, montmorillonite, $SiO_2$—$TiO_2$, tungstated $ZrO_2$, zeolites, $V_2O_5$, $MoO_3$, or mixtures thereof. In one embodiment, the solid support comprises $SiO_2$. In other embodiments, it may be desirable to not have a solid support.

The catalysts utilized in the processes described herein can be synthesized according to various methods. For example, a copper or copper oxide-containing material can be mixed with a solution of the heteropoly acid component, the solvent (e.g., water) evaporated to dryness, and the resulting powder calcined. Alternatively, the heteropoly acid component may itself be provided as a solution of heteropolyacid and a basic salt, for example, a solution containing a mixture of $H_3[P(W_3O_{10})_4]$ and cesium carbonate in suitable proportions to form $Cs_{2.5}H_{0.5}[P(W_3O_{10})_4]$. In another catalyst preparation method, a copper or copper oxide-containing material is physically mixed with a heteropoly acid or with a partially cesium-exchanged heteropoly acid.

Catalyst preparation may further comprise drying catalyst materials under elevated temperatures from 30-250° C., preferably 50-150° C.; and/or calcination by heating in the presence of air at temperatures from 250-800° C., preferably 300-450° C.; and optionally reduction in the presence of hydrogen at 100-400° C., preferably 200-300° C., or reduction with alternative reducing agents such as hydrazine, formic acid or ammonium formate. The above techniques may be utilized with powdered or formed particulate catalyst materials prepared by tableting, extrusion or other techniques common for catalyst synthesis. Where powdered catalysts materials are utilized, it will be appreciated that the catalyst support or the resulting catalyst material may be sieved to a desired particle size and that the particle size may be optimized to enhance catalyst performance.

Catalysts comprising Cu and/or CuO and at least one oxide as described above can be prepared by forming a co-precipitated catalyst comprising compounds which are thermally decomposable to oxides or mixed oxides.

The precipitated catalyst can be formed by admixing solutions of the elements and heating the resultant mixture to its precipitation temperature; separately heating a solution of a precipitant in water; and thereafter adding both solutions to preheated demineralized water with vigorous stirring and strict pH control, for example in a precipitation reactor. Alternatively, the precipitate can be formed by admixing solutions of the elements and heating the resultant mixture to its precipitation temperature; then adding the preheated mixture or solution of elements rapidly to a predetermined volume of a preheated solution of a precipitant in water. In yet another method of forming a precipitated catalyst, the precipitate can be formed by admixing solutions of the elements and heating the resultant mixture to its precipitation temperature; then adding a preheated solution of precipitant in water (preheated to a predetermined precipitation temperature) to the hot solution or mixture of the elements with vigorous stirring, until the desired pH value of combined solutions is reached. In all methods, the precipitant can be a solution of sodium, potassium and/or ammonium carbonate or bicarbonate in water.

The precipitation can be carried out at high temperature, for example between about 75° C. and 100° C. Lower temperatures, for example between about 50° C. and 60° C., can also be used, but the crystallite size of the catalyst precursor so formed is larger, and the activity of such a catalyst may be lower. The precipitation can be effected at a pH in the range of 6.5-9.5.

After maintaining the stirred solution at the precipitation temperature for a period of time between about 0.5 and 60 minutes, the precipitate can then be separated from the residual liquid. The separation can be effected by filtration. The precipitate can be re-suspended at least once, but typically a few times, in demineralized water, then separated from the water by filtration, and finally washed thoroughly on the filter.

The washed precipitate comprising a homogeneous hydrated catalyst precursor can then be dried by any known drying process, for example in an oven at temperatures between 50° C. and 130° C., under vacuum or at normal pressure. Alternatively, spray drying can be employed.

The dried precipitate, also referred to herein as a precursor, comprises an essentially homogeneous association of carbonates and hydroxycarbonates with a potential oxide content of between 65% and 80%. As described above herein, the elements may initially be in soluble nitrate form or optionally in the form of a thermally decomposable ammonium salt. The dried precipitate can be calcined to provide a catalyst.

The calcination can comprise treating the dried precipitate at a temperature of between 200° C. and 450° C., for example between 250° C. and 350° C., for between 3 and 10 hours, to obtain a homogeneous catalyst.

The homogeneous catalyst can be densified and pelletized after addition of 1-3 wt %, for example about 2 wt %, graphite. It can also be made into extrudates using, for example, methyl cellulose as a binder. The homogeneous catalyst can also be sieved to a desired particle size distribution to be used in batch or continuous stirred tank reactors.

The copper component of the active catalyst contains the copper in a dispersed form, and after activation acts primarily as the active constituent of the catalyst, while the additional oxide component(s) acts primarily, but not exclusively, as a structural support. An oxide of chromium, zinc, manganese, or barium when present, thus enhances the activity and/or selectivity of the catalyst and its resistance to poisons, while aluminum oxide, zirconium oxide, and silica enhances the stability, abrasion or attrition resistance, mechanical strength, and thermal stability of the active catalyst.

The active catalyst can be reduced by thermal activation to produce an active catalyst in which at least a portion of the copper and other element(s) present in the catalyst are in metallic form.

The thermal activation can comprise reduction treatment of the calcined catalyst in a reactor, using a mixture of an inert gas, preferably nitrogen, and at least one reducing gas, such as hydrogen, carbon monoxide or a mixture thereof. The molar ratio between reducing gas and inert gas should be between 1:30 and 1:100. The reduction temperature can be between 100° C. to 280° C., preferably between 130° C. and 240° C., and the pressure can be 0.1 to 1 MPa.

The catalyst is preferably first slowly heated at a rate of between 30-50° C./hour under the inert gas at a pressure between 0.6-0.9 MPa, until a temperature between 120° C. and 150° C. has been reached. Thereafter the reduction takes place by adding the reducing gas to the inert gas in a molar ratio as described above, but preferably between 1:50 and 1:40. The temperature is then slowly further increased at a rate of 15-25° C./hour to reach a temperature between 190 C.° and 210° C. The thermal reductive activation is continued at this temperature for a time period of between 10 and 24 hours. Thereafter, in a final step, the temperature can be increased to between 230° C. and 250° C. and the molar ratio of reducing gas to inert gas adjusted to between 1:10 and 1:6 for a time period of 1-3 hours, in order to complete activation. The reduced catalyst can then be stabilized by passivating the catalyst in a mixture of nitrogen and oxygen to prevent complete oxidation of the catalyst when exposed to air.

In another embodiment, a wide range of commercially available catalyst supports comprising metal oxides, mixed metal oxides or metal-incorporated metal oxides (such as gamma-alumina, La-doped alumina, Ce-doped zirconia, magnesium oxide, and USY zeolite) can be used as supports with the CuO catalyst.

The metals so incorporated in the metal oxide or mixed metal oxide support can be an alkali, an alkaline earth metal, a rare earth metal, or a mixture of one or more such metals. Incorporation of the specified metal or metals onto the metal oxide or mixed metal oxide support can be accomplished by impregnating the support with an aqueous solution of water-soluble salt precursor(s) of metal(s) such as nitrates and acetates by known methods, drying the wetted support, and then calcining the combination of the metal salt(s) and metal oxide or mixed metal oxide support at a temperature of 350° C. up to 600° C. for about 2 to 16 hours to produce a metal-modified metal oxide or mixed metal oxide support(s). The calcining step at 250° C. to 600° C. prior to depositing the copper on the support is necessary. The time of calcining should be sufficient to decompose the metal salt(s) to the metal oxide(s). The total amount of added metal(s) in the support is in the range of 0.5% to 20% by weight, based upon the weight of the support.

After incorporation of the metal(s), copper, preferably as copper nitrate, is impregnated on the metal-modified metal oxide or mixed metal oxide support. The amount of copper deposited will depend on the desired activity of the catalyst, and can be as little as 2% by weight to as much as 20% by weight. The final catalyst composition containing the copper catalyst on the modified support can be in the form of powder, granules, extrudates or tablets, but certain specific characteristics such as surface area and pore volume, for example, are modified by reason of the deposit of copper.

In another embodiment, the catalyst comprising active metal(s) in the co-precipitated form with other elements, or active metal(s) dispersed on a first oxide, mixed metal oxides or metal-modified metal oxide support, as described herein above, can be either physically mixed and sieved to appropriate size, or intimately mixed and optionally co-extruded or pelletized with a second metal oxide, mixed metal oxides or metal-modified metal oxide support. The pelletized or co-extruded catalyst can be optionally crushed and sieved to appropriate size for use in slurry batch, continuous stirred tank, or fixed bed reactors.

The catalyst can be in any physical form typical for heterogeneous catalysts, including but not limited to: powdered (also known as "fluidized") forms with 0.01-150 μm particle size, formed tablets, extrudates, spheres, engineered particles having uniform 0.5-10 mm size, monolithic structures on which surfaces the catalyst is applied, or combinations of two or more of the above.

Examples of $C_n$ oxygenates that are suitable for use in the present processes include 1,2,6-hexanetriol; 1,2,5-pentanetriol; 2H-tetrahydropyran-2-methanol; tetrahydrofuran-2,5-dimethanol; furan-2,5-dimethanol; 2,5 dihydrofuran-2,5-dimethanol; levoglucosenone; levoglucosan; levoglucosenol; 1,6-anhydro-3,4-dideoxy-p-D-pyranose-2-one; isosorbide; hydroxymethylfurfural; sorbitol; glucose; fructose; xylitol; 3,4-dihydro-2H-pyran-2-carbaldehyde; 1,2,5,6-hexanetetraol; 1,2,3,5,6-hexanepentanol; 1,5-anhydro-3,4-dideoxyhexitol; 5-hydroxy-2H-tetrahydropyran-2 methanol; furfural; furfuryl alcohol; tetrahydrofurfuryl alcohol; pentoses; dimers containing pentose; oligomers containing pentose; hexoses; dimers containing hexose; oligomers containing hexose; condensation products from the reaction of 5-(hydroxymethyl)-2-furfural ("HMF") with ketones and/or aldehydes, and condensation products from the reaction of furfural with ketones and/or aldehydes. The feedstock may comprise one or more Cn oxygenates.

In one embodiment, the $O_n$ oxygenate comprises 1,2,6-hexanetriol; 2H-tetrahydropyran-2-methanol; tetrahydrofuran-2,5-dimethanol; levoglucosenone; 3,4-dihydro-2H-pyran-2-carbaldehyde, or mixtures thereof. These $O_n$ oxygenates are useful for preparation of reaction mixtures comprising 1,6-hexanediol by the processes disclosed herein. In one embodiment, the $O_n$ oxygenate comprises 1,2,6-hexanetriol.

In one embodiment, the $O_n$ oxygenate comprises 1,2,5-pentanetriol; furfural; furfuryl alcohol; tetrahydrofurfuryl alcohol; xylitol; or mixtures thereof. Such $O_n$ oxygenates are useful for preparation of product mixtures comprising 1,5-hexanediol by the processes disclosed herein. Examples of suitable pentoses include without limitation xylose, arabinose, lyxose, xylitol, and ribose. Examples of suitable hexoses include without limitation glucose, mannose, fructose, and galactose. Examples of condensation products from the reaction of furfural or 5-(hydroxymethyl)-2-furfural with ketones and/or aldehydes are described in Synthesis (2008), (7), 1023-1028 (e.g., CAS Reg. No. 1040375-91-4 and CAS Reg. No. 886-77-1); and in ChemSusChem (2010), 3(10), 1158-1161, in which subjecting furfural and 5-(hydroxymethyl)-2-furfural to aldol condensation produced molecules having 8 to 15 carbon atoms.

Suitable $C_n$ oxygenates can be derived from biorenewable resources including biomass. Biomass may be derived from a single source, or biomass can comprise a mixture derived from more than one source; for example, biomass could comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste or a combination thereof. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, and animal manure or a combination thereof. Biomass that is useful for the invention may include biomass that has a relatively high carbohydrate value, is relatively dense, and/or is relatively easy to collect, transport, store and/or handle. In one embodiment, the $C_n$ oxygenate is ultimately derived from corn cobs, sugar cane bagasse, switchgrass, wheat straw, sawdust and other wood waste, and lignocellulosic feedstocks.

A biorenewable resource such as biomass can be pyrolyzed under high temperature conditions in the presence of an acid catalyst to provide useful chemical intermediates. For example, pyrolysis of wood, starch, glucose or cellulose can produce levoglucosenone by known and conventional methods (see, for example, Ponder (*Applied Biochemistry and Biotechnology*, Vol 24/25, 41-41 (1990)) or Shafizadeh (*Carbohydrate Research*, 71, 169-191 (1979)).

Glycerol can be obtained from a biorenewable resource, for example from hydrolysis of vegetable and animal fats and oils (that is, triacylglycerides comprising ester functionality resulting from the combination of glycerol with $C_{12}$ or greater fatty acids). 1,2,6-Hexanetriol can be obtained from materials such as glucose, cellulose or glycerol derived from a biorenewable resource. For example, 1,2,6-hexanetriol can be obtained by a process comprising the steps of contacting glycerol with a catalyst to prepare acrolein, heating acrolein (optionally in the presence of a catalyst) to prepare 2-formyl-3,4-dihydro-2H-pyran, contacting 2-formyl-3,4-dihydro-2H-pyran with water to prepare 2-hydroxyadipic aldehyde and contacting 2-hydroxyadipic aldehyde with hydrogen and a catalyst to produce a product mixture comprising 1,2,6-hexanetriol. See, for example, U.S. Pat. No. 2,768,213, German Patent No. 4238493, and L. Ott, et al. in *Green Chem.*, 2006, 8, 214-220.

The catalyst may be present in any weight ratio to the feedstock sufficient to catalyze the selective hydrodeoxygenation, generally in the range of 0.0001:1 to 1:1, preferably 0.001:1 to 0.5:1 for batch reactions. For continuous reactions, the same ratios are appropriate where the weight ratio of feed to catalyst is defined as weight of $O_n$ oxygenate feed processed per weight of catalyst.

Useful temperatures for the processes are between about 30° C. and about 300° C. In some embodiments, the temperature is between and optionally includes any two of the following values: 30° C., 40° C., 50° C., 60° C., 70° C., 80° C., 90° C., 100° C., 110° C., 120° C., 130° C., 140° C., 150° C., 160° C., 170° C., 180° C., 190° C., 200° C., 210° C., 220° C., 230° C., 240° C., 250° C., 260° C., 270° C., 280° C., 290° C., and 300° C. It is expected that with some catalysts, temperatures above about 300° C. could be used.

The process is conducted by contacting a Cn oxygenate feed with hydrogen in the presence of the catalyst for a time sufficient to form a product mixture comprising an $\alpha,\omega$—$C_n$-diol. The mole ratio of hydrogen to feed is not critical as long as sufficient hydrogen is present to produce the desired $\alpha,\omega$-$C_n$-diol. Hydrogen is preferably used in excess, and may optionally be used in combination with an inert gas such as nitrogen or argon. If an inert gas is used in combination with the hydrogen, the amount of the inert gas should be such that it does not negatively impact the formation of the product mixture. The pressure of the process may be between about 300 kPa and about 25,000 kPa. In some embodiments, the pressure of the process is between and optionally includes any two of the following values: 300; 500; 1000; 1500; 2000; 2500; 3000; 3500; 4000; 4500; 5000; 10,000; 15,000; 20,000; and 25,000 kPa.

The process is typically conducted in the presence of a solvent, which may serve to reduce the viscosity of the system to improve fluidity of the catalyst in the reaction vessel and/or to remove the heat of reaction and improve the performance of the process. Polar solvents are preferred. The solvent may be present in a range of 1% to 95% by weight of the total reaction mixture, excluding the catalyst.

The reaction products may be isolated or purified by any common methods known in the art including but not limited to distillation, wiped film evaporation, chromatography, adsorption, crystallization, and membrane separation.

It will be appreciated that the processes disclosed herein can also be utilized to prepare useful intermediates or byproducts in the synthesis of the $\alpha,\omega$-diols through optimization of the process parameters. Examples of intermediates that can be prepared during synthesis of 1,5-pentanediol and/or 1,6-hexanediol include but are not limited to furan dimethanol: tetrahydrofuran dimethanol; tetrahydropyran-2-methanol; levoglucosanol; and furfuryl alcohol. Examples of byproducts which can be obtained during synthesis of 1,5-pentanediol and/or 1,6-hexanediol include but are not limited to isomeric hexanols; isomeric pentanols; 1,5-hexanediol; 1,2-hexanediol; 2-methyltetrahydropyran; 2,5-dimethyltetrahydrofuran; 1,2-cyclohexanediol; 1,2-cyclopentanediol; cyclohexanol, and mixtures thereof.

The $\alpha,\omega$-$C_n$-diols obtained by the processes disclosed herein can be converted to industrially useful materials such as $\alpha,\omega$-$C_n$-diaminoalkanes. For example, 1,5-pentanediol and 1,6-hexanediol can be reductively aminated to 1,5-pentanediamine (1,5-diaminopentane) and 1,6-hexanediamine (1,6-diaminohexane), respectively, by methods known in the art. See, for example, U.S. Pat. No. 3,215,742; U.S. Pat. No. 3,268,588; and U.S. Pat. No. 3,270,059.

In some embodiments, the processes disclosed herein further comprise the steps:

(c) optionally, isolating the $\alpha,\omega$-$C_n$-diol from the product mixture;

(d) contacting the $\alpha,\omega$-$C_n$-diol with ammonia and hydrogen in the presence of a reductive amination catalyst at a temperature and for a time sufficient to form a second product mixture comprising an $\alpha,\omega$-$C_n$-diaminoalkane; and (e) optionally, isolating the $\alpha,\omega$-$C_n$-diaminoalkane from the second product mixture.

In one embodiment, the $\alpha,\omega$-$C_n$-diaminoalkane comprises 1,6-diaminohexane. In one embodiment, the $\alpha,\omega$-$C_n$-diaminoalkane comprises 1,5-diaminopentane.

The reductive amination catalyst contains at least one element selected from Groups IB, VIIB, VIIB, and VIII of the Periodic Table, for example iron, cobalt, nickel, ruthenium, rhodium, palladium, osmium, copper, chromium, iridium, or platinum. The elements may be in the zero oxidation state or in the form of a chemical compound. The reductive amination catalyst may be supported, unsupported or Raney-type. In one embodiment, the reductive amination catalyst contains ruthenium. In one embodiment, the reductive amination catalyst contains nickel. In one embodiment, the reductive amination catalyst is Raney nickel. In one embodiment, the reductive amination catalyst is Raney copper. In one embodiment, the reductive amination catalyst is Raney cobalt.

The reductive amination step is conducted by contacting the $\alpha,\omega$-$C_n$-diol, or a product mixture comprising the $\alpha,\omega$-$C_n$-diol, with ammonia and hydrogen in the presence of the catalyst for a time sufficient to form a second product mixture comprising an $\alpha,\omega$-$C_n$-diaminoalkane. Useful temperatures for the reductive amination step are in the range of about 40° C. to 300° C., for example in the range of about 75° C. to 150° C. Typically pressures are in the range of about 2 MPa to 35 MPa, for example in the range of about 4 MPa to 12 MPa. The molar ratio of hydrogen to the $\alpha,\omega$-$C_n$-diol is typically equal to or greater than 1:1, for example in the range of 1:1 to 100:1, or in the range of 1:1 to 50:1.

The reductive amination step is typically performed in liquid ammonia solvent. The ammonia is used in stoichiometric excess with reference to the $\alpha,\omega$-$C_n$-diol. Typically, a molar ratio of 1:1 to 80:1 of ammonia to the α,ω-C$_n$-diol can be used, for example a molar ratio in the range of 10:1 to 50:1. Optionally, an additional solvent such as water, methanol, ethanol, butanol, pentanol, hexanol, an, ester, a hydrocarbon, tetrahydrofuran, or dioxane, can be used. The weight ratio of the additional solvent to the α,ω-C$_n$-diol is typically in the range of 0.1:1 to 5:1.

The reductive amination step can be performed in a fixed bed reactor or in a slurry reactor, for example a batch, continuous stirred tank reactor or bubble column reactor. The α,ω-C$_n$-diamine may be isolated from the second product mixture by any common methods known in the art, for example fractional distillation under moderate vacuum.

EXAMPLES

The processes described herein are illustrated in the following examples. From the above discussion and these examples, one skilled in the art can ascertain the essential characteristics of this invention, and without departing from the spirit and scope thereof, can make various changes and modifications to adapt it to various uses and conditions.

The following abbreviations are used in the examples: "° C." means degrees Celsius; "wt %" means weight percent; "g" means gram; "mg" means milligrams; "m$^2$/g" means square meters per gram; "psi" means pounds per square inch; "mL" means milliliter; "M" means mole/liter; "mL/min" means milliliter(s) per minute; "h" means hour(s); "kPa" means kilopascal; "GC" means gas chromatography; "Temp" means temperature; "Ex" means Example, "Comp Ex" means Comparative Example; "cony" means conversion; "GC" means gas chromatography; "MS" means "mass spectrometry"; "12HD" means 1,2-hexanediol; "12CHD" means 1,2-cyclohexanediol; "1H" means 1-hexanol.

Percent conversion and percent yield are defined as follows, where the mol of compounds are determined from calibrated gas chromatographic methods:

$$\% \text{ Conversion} = \frac{100 * (\text{mol starting material charged} - \text{mol starting material remaining})}{\text{mol starting material charged}}$$

$$\% \text{ Yield} = \frac{100 * \text{mol product compound}}{\text{mol starting material charged}}$$

Materials Cs$_2$CO$_3$, H$_3$PW$_{12}$O$_{40}$.(H$_2$O)$_x$, H$_4$SiW$_{12}$O$_{40}$.(H$_2$O)$_x$ and tetraammineplatinum (II) nitrate were purchased from Sigma-Aldrich (St. Louis, Mo.). Copper(II) nitrate hydrate and ammonium tungsten oxide hydrate were purchased from Alfa Aesar (Ward Hill, Mass.). 1,2,6-Hexanetriol (greater than 97 GC area % purity) was obtained from Evonik DEGUSSA GmBH, Marl, Germany. Tetrahydrofuran-2,5-dimethanol (97% purity) was obtained from Aldrich. 2-Hydroxymethyltetrahydropyran (98% purity) was obtained from Aldrich.

The materials listed in Table 1 were used to prepare the catalyst compositions used in the hydrodeoxygenation Examples 5-30. All catalysts were calcined in air unless indicated otherwise.

TABLE 1

Some Commercially Available Materials Used in Preparation of Selected Catalysts

| Material Identifier | Description | Vendor | Catalog Number | Composition (wt %) |
|---|---|---|---|---|
| A | BaO/CuO/Cr$_2$O$_3$ | SuedChemie | G-22 | CuO 41%, Cr$_2$O$_3$ 43%, BaO 12% |
| B | CuO/Cr$_2$O$_3$ | SuedChemie | T-4466 | CuO 53%, Cr$_2$O$_3$ 45% |
| C | CuO/MnO$_2$ | SuedChemie | T-4489 | CuO 56%, MnO$_2$ 10%, Al$_2$O$_3$ 34% |
| D | CuO/ZnO/Al$_2$O$_3$ | SuedChemie | ActiSorb ®301 | CuO 53%, ZnO 27%, Al$_2$O$_3$ 20% |
| E | CuO/ZnO | SuedChemie | T-2130 | CuO 33%, ZnO 66% |
| F | CuO/Cr$_2$O$_3$/MnO$_2$ | BASF | Cu-1950P | Copper Chromite 73%, Copper Oxide 21%, Manganese Oxide 5%, Chromium (6+) <0.3% |
| G* | CuO/SiO$_2$ (BASF Cu-0860) | BASF | Cu-0860 | Decan-1-ol 30.0-50.0%, Copper 25.0-40.0%, Silicon dioxide 10.0-20.0%, Calcium oxide 0.0-10.0%, Copper oxide 0.0-10.0%, Palygorskite 7 0.0-7.0%, Crystalline silica 0.0-1.0% |

TABLE 1-continued

Some Commercially Available Materials Used in Preparation of Selected Catalysts

| Material Identifier | Description | Vendor | Catalog Number | Composition (wt %) |
|---|---|---|---|---|
| H* | CuO/SiO$_2$ (Evonik CPCAT 9/1593) | Evonik | CPCAT 9/1593 | CuO 0-40%, Cu$_2$O 0-40%, Na$_2$O$_3$Si 0-5%, SiO$_2$ >40% |

*supported Cu catalysts

Example 1

Preparation of catalyst by treating CuO/SiO$_2$ with H$_3$[P(W$_3$O$_{10}$)$_4$]

In a round bottomed flask about 6.27 g of CuO/SiO$_2$ (BASF Cu-0860) was combined with a solution of 6.29 g phosphotungstic acid hydrate H$_3$[P(W$_3$O$_{10}$)$_4$] (Aldrich catalogue number P4006) dissolved in about 50 mL water. The flask was attached to a rotary evaporator at atmospheric pressure and rotated for 15 min at 25° C. The temperature was raised to about 40° C. and the water was removed by applying vacuum for about 2 h before the temperature was raised to 80° C. for an additional 12 h. The remaining powder was calcined in air at 350° C. for about 12 h.

Example 2

Preparation of catalyst by treating CuO/SiO$_2$ with H$_4$[Si(W$_3$O$_{10}$)$_4$]

This example was conducted as for Example 1 but silicotungstic acid hydrate H$_4$[Si(W$_3$O$_{10}$)$_4$] (Aldrich catalogue number 3833416) was used instead of phosphotungstic acid hydrate.

Example 3

Dried Cs$_2$CO$_3$ (2.03 g) (Aldrich) (300° C., 6 h, vacuum) was dissolved in 25 mL of water and about 3.5 mL (1.72 mmol Cs atom) were added to a stirred mixture of 2.3 g (0.71 mmol) of dry (60° C., 2 h 150 Torr vacuum) phosphotungstic acid: H$_3$[P(W$_3$O$_{10}$)$_4$] (Aldrich order number P4006) in about 15 mL water and 2.2 g of CuO/SiO$_2$ (BASF Cu-0860). The flask was attached to a rotary evaporator at atmospheric pressure and rotated for 15 min at 25° C. The temperature was raised to about 60° C. and the water was removed by applying vacuum for about 1 h before it was dried in a vacuum oven at 120° C. (150 Torr) for about 2 h. The remaining powder was calcined in air at 300° C. for about 2 h.

Example 4

Catalyst Performance

Selective Hydrodeoxygenation of 1,2,6-Hexanetriol

In a 20 mL stainless steel (Hastalloy) pressure reactor equipped with a magnetic stir bar 9.5 mL of water were added to 500 mg of 1,2,6-hexanetriol (~98% pure) and about 500 mg of the catalyst of Example 1. The reactor was closed and connected to a high pressure gas manifold and the content was purged with nitrogen gas (1000 psi) 3 times before hydrogen was added. About 800 psig (5516 kPa) of hydrogen were added and the reactor was heated to 200° C. for 2 h followed by 4 h at 260° C. to reach a final pressure of approximately 1100 psig (7584 kPa). After 4 h at 260° C. the reactor was allowed to cool to room temperature within 2 h and depressurized. The reaction solution was diluted with n-propanol and an internal standard, filtered through a standard 5 micron disposable filter, and a sample was taken and analyzed by GC and GC/MS. Products were identified by matching retention times and mass spectra using authentic samples. The conversion of 1,2,6 hexanetriol was about 94%. The yield of 1,6-hexanediol was about 61%, the yield of 2H-tetrahydropyran-2-methanol was about 22%, the yield of 1,2-hexanediol was about 6%, with the balance (about 10%) consisting of by-product alcohols and ethers.

Preparation of Partially Cesium-Exchanged Heteropoly Acid Cs$_{2.5}$H$_{0.5}$PW$_{12}$O$_{40}$ The partially Cs-exchanged salt of the tungsten heteropoly acid was prepared using an aqueous solution of Cs$_2$CO$_3$ and an aqueous solution of H$_3$PW$_{12}$O$_{40}$. The heteropolyacid H$_3$PW$_{12}$O$_{40}$ was prepared for use in aqueous solution by first dehydrating it at 60° C. under vacuum for 2 hours. Cs$_2$CO$_3$ was dehydrated at 420° C. for 2 hours under vacuum prior to its use for preparing an aqueous solution.

An aqueous solution of H$_3$PW$_{12}$O$_{40}$ (0.08 mol/L) was titrated with an aqueous solution of Cs$_2$CO$_3$ (0.25 mol/L) at room temperature at a rate of 1 mL/minute. The resulting white colloidal suspension was evaporated to a solid at 50° C. under vacuum. The solids were then placed in a 120° C. vacuum oven for 2 hours to remove water. The dried solids were calcined in air at 300° C. for 1 hour.

The partially Cs-exchanged heteropoly acid Cs$_{2.5}$H$_{0.5}$PW$_{12}$O$_{40}$ was used as described below in Catalyst Preparation Method A to prepare catalysts comprising a first metal component, a heteropoly acid component, at least one promoter, and optionally a support.

Preparation of Partially Cesium-Exchanged Heteropoly Acid Cs$_{2.5}$H$_{0.5}$SiW$_{12}$O$_{40}$ The partially Cs-exchanged salt of the tungsten heteropoly acid was prepared as described above except that H$_4$SiW$_{12}$O$_{40}$ was used in place of H$_3$PW$_{12}$O$_{40}$. The partially Cs-exchanged heteropoly acid Cs$_{2.5}$H$_{0.5}$SiW$_{12}$O$_{40}$ was used as described below in Catalyst Preparation Method A to prepare catalysts comprising a first metal component, a heteropoly acid component, at least one promoter, and optionally a support.

Preparation of Partially Cesium-Exchanged Heteropoly Acid Cs$_{2.5}$H$_{0.5}$PW$_{12}$O$_{40}$ (15% wt) on SiO$_2$ The partially Cs-exchanged salt of the tungsten heteropoly acid was prepared using an aqueous solution of Cs$_2$CO$_3$, and SiO$_2$ (Silica Gel 60, EMD, Darmstadt Germany) suspended in an aqueous solution of H$_3$PW$_{12}$O$_{40}$. The heteropoly acid H$_3$PW$_{12}$O$_{40}$ was prepared for use in aqueous solution by first dehydrating it at 60° C. under vacuum for 2 hours. Cs$_2$CO$_3$ was dehydrated at 420° C. for 2 hours under vacuum prior to its use for preparing an aqueous solution, and SiO$_2$ was used as received.

SiO$_2$ (83.1 wt. parts) was suspended in a solution of 13.2 wt. parts of H$_3$PW$_{12}$O$_{40}$ in water (0.08 mol/L). This suspension was titrated with a solution of 3.7 wt. parts Cs$_2$CO$_3$ (0.25 mol/L) in water at room temperature at a rate of 1 mL/minute. The resulting white colloidal suspension was evaporated to a solid at 50° C. under vacuum. The solids were then placed in a 120° C. vacuum oven for 2 hours to remove water. The dried solids were calcined in air at 300° C. for 1 hour. The material was used as described below in Catalyst Preparation Method E.

Catalyst Preparation Method A

Preparation of Catalysts by Physically Mixing Supported or Unsupported Copper Oxide Catalysts with a Heteropoly Acid or Partially Cesium-Exchanged Heteropoly Acid Selected catalysts were prepared by physically mixing a supported or non-supported copper oxide catalyst with a heteropoly acid or a partially Cs-exchanged heteropoly acid according to the following procedure.

A pre-determined amount of a dry supported or unsupported copper oxide catalyst (CuO/MnO$_2$/Al$_2$O$_3$, BaO/CuO/Cr$_2$O$_3$/SiO$_2$, BaO/CuO/MnO$_2$/Cr$_2$O$_3$, or CuO/SiO$_2$) was combined with a pre-determined amount of a dry heteropoly acid (H$_3$PW$_{12}$O$_{40}$ or H$_4$SiW$_{12}$O$_{40}$), or a dry partially Cs-exchanged heteropoly acid (Cs$_{2.5}$H$_{0.5}$PW$_{12}$O$_{40}$ or Cs$_{2.5}$H$_{0.5}$SiW$_{12}$O$_{40}$) prepared as described above, in a mortar. The pre-determined amount of each component was chosen so as to provide the desired weight ratio of each component in the resulting catalyst composition. The mixture was ground with a pestle for about 5 minutes. The catalyst mixture was then calcined at 300° C. (1 hour) and stored under an inert gas atmosphere. The yield of each catalyst composition was approximately quantitative.

The catalysts prepared according to Method A were used in Examples 5-15. Results are presented in Table 2.

Catalyst Preparation Method B

Preparation of Catalysts by In Situ Precipitation of Partially Cesium-Exchanged Heteropoly Acids on Supports or Supported Copper Oxide Catalysts Selected catalysts comprising partially Cs-exchanged heteropoly acids Cs$_{2.5}$H$_{0.5}$PW$_{12}$O$_{40}$ and Cs$_{2.5}$H$_{0.5}$SiW$_{12}$O$_{40}$ were prepared by mixing a copper oxide catalyst in an aqueous heteropoly acid solution then precipitating the heteropoly acid with Cs$_2$CO$_3$ according to the following procedure.

The heteropoly acid H$_3$PW$_{12}$O$_{40}$ or H$_4$SiW$_{12}$O$_{40}$ was prepared for use in aqueous solution by first dehydrating it at 60° C. under a vacuum for 2 hours. Cs$_2$CO$_3$ was dehydrated at 420° C. for 2 hours under a vacuum prior to its use for preparing an aqueous solution.

A pre-determined amount of a supported or unsupported copper oxide catalyst (CuO/MnO$_2$/Al$_2$O$_3$, BaO/CuO/Cr$_2$O$_3$/SiO$_2$, BaO/CuO/MnO$_2$/Cr$_2$O$_3$, or CuO/SiO$_2$) was first suspended in an aqueous solution of H$_3$PW$_{12}$O$_{40}$ (0.08 mol/L) or H$_4$SiW$_{12}$O$_{40}$ (0.08 mol/L). The pre-determined amount of the supported metal catalyst was chosen so as to provide one part by weight of the copper oxide catalyst to one part by weight of Cs$_{2.5}$H$_{0.5}$PW$_{12}$O$_{40}$ or Cs$_{2.5}$H$_{0.5}$SiW$_{12}$O$_{40}$ in the prepared catalyst composition. This mixture was then titrated with an aqueous solution of Cs$_2$CO$_3$ (0.25 mol/L) at room temperature at a rate of 1 mL/minute. The resulting white colloidal suspension was evaporated to a solid at 50° C. under a vacuum. The solids were then placed in a 120° C. vacuum oven for 2 hours to remove water. The dried solids were calcined in air at 300° C. for 1 hour.

The catalysts prepared according to Method B were used in Examples 16-28. Results are presented in Table 3.

Examples 5-28

Hydrodeoxygenation of 1,2,6-Hexanetriol Using Prepared Catalysts

In Example 5 through Example 28, catalysts prepared as described above were used in hydrodeoxygenation reactions to convert 126HT to a product mixture comprising 16HD.

Each Example was performed as follows. A 5% wt solution of 126HT in water was combined with about 50 mg of the desired catalyst (see Tables 2 and 3) in a glass vial equipped with a magnetic stir bar. The vial was capped with a perforated septum to limit vapor transfer rates. Next, the capped vial was placed in a stainless steel (SS316) parallel pressure reactor having 8 individual wells. The reactor was then connected to a high pressure gas manifold and purged with nitrogen gas (1000 psi, 6895 kPa) three times. About 800 psi (5516 kPa) of hydrogen was then added and the reactor was heated to the desired temperature indicated in Table 2 or Table 3; the hydrogen pressure in the reactor was adjusted to about 1000 psi (6895 kPa). These conditions were held for 4 hours.

The reactor was then allowed to cool to room temperature and the pressure was released. Each reaction solution was diluted with n-propanol containing an internal standard, filtered through a 5-micron disposable filter, and analyzed by GC (and in some cases by GC/MS) using an internal standard method for quantitative analysis.

Hydrodeoxygenation results for catalysts made by Catalyst Preparation Method A are provided in Table 2.

Hydrodeoxygenation results for catalysts made by Catalyst Preparation Method B are provided in Table 3.

Comparative Examples A-H

Comparative Examples A-H were carried out as for Examples 5-28 except using catalysts comprising a first metal and no heteropoly acid component, or catalysts comprising a heteropoly acid component with no metal component. Results are given in Table 4.

TABLE 2

Hydrodeoxygenation Results for Catalysts made by Catalyst Preparation Method A

| Ex | Temp (° C.) | First Metal Component (Component A) | Heteropoly Acid (Component B) | Ratio A:B (wt) | Conv (%) | Yield (%) 16HD | THPM | 12HD | 12CHD* |
|---|---|---|---|---|---|---|---|---|---|
| 5 | 260 | CuO/SiO$_2$ (i) | H$_3$SiW$_{12}$O$_{40}$ | 1:1 | 92 | 25 | 26 | 10 | <1 |
| 6 | 250 | CuO/SiO$_2$ (i) | H$_3$SiW$_{12}$O$_{40}$ | 1:1 | 90 | 30 | 24 | 3 | <1 |

TABLE 2-continued

Hydrodeoxygenation Results for Catalysts made by Catalyst Preparation Method A

| Ex | Temp (°C.) | First Metal Component (Component A) | Heteropoly Acid (Component B) | Ratio A:B (wt) | Conv (%) | Yield (%) 16HD | THPM | 12HD | 12CHD* |
|---|---|---|---|---|---|---|---|---|---|
| 7  | 220 | CuO/SiO$_2$ (i)         | H$_3$SiW$_{12}$O$_{40}$        | 1:1 | 37  | 13 | 14 | 4  | 1  |
| 8  | 250 | CuO/SiO$_2$ (i)         | H$_3$PW$_{12}$O$_{40}$         | n/a | 59  | 18 | 18 | 1  | 7  |
| 9  | 260 | CuO/SiO$_2$ (i)         | Cs$_{2.5}$H$_{0.5}$PW$_{12}$O$_{40}$ | 1:1 | 28  | 2  | 8  | 1  | <1 |
| 10 | 260 | CuO/MnO$_2$/Al$_2$O$_3$ | Cs$_{2.5}$H$_{0.5}$PW$_{12}$O$_{40}$ | 1:1 | 57  | 8  | 11 | 5  | <1 |
| 11 | 260 | CuO/Cr$_2$O$_3$/MnO$_2$ | Cs$_{2.5}$H$_{0.5}$PW$_{12}$O$_{40}$ | 1:1 | 100 | 5  | 20 | 14 | <1 |
| 12 | 260 | BaO/CuO/Cr$_2$O$_3$     | Cs$_{2.5}$H$_{0.5}$PW$_{12}$O$_{40}$ | 1:1 | 53  | 2  | 11 | 8  | <1 |
| 13 | 260 | CuO/SiO$_2$ (ii)        | Cs$_{2.5}$H$_{0.5}$PW$_{12}$O$_{40}$ | 1:1 | 100 | 21 | 22 | 5  | <1 |
| 14 | 260 | CuO/Cr$_2$O$_3$         | Cs$_{2.5}$H$_{0.5}$PW$_{12}$O$_{40}$ | 1:1 | 100 | 8  | 17 | 12 | <1 |
| 15 | 260 | CuO/ZnO/Al$_2$O$_3$     | Cs$_{2.5}$H$_{0.5}$PW$_{12}$O$_{40}$ | 1:1 | 80  | 3  | 14 | 14 | <1 |

*12CHD yield reported as the sum of cis- and trans- isomers
(i) CuO/SiO$_2$ obtained from BASF
(ii) CuO/SiO$_2$ obtained from Evonik
n/a means not available

TABLE 3

Hydrodeoxygenation Results for Catalysts made by Catalyst Preparation Method B

| Ex | Temp °C. | First Metal Component (Component A) | Heteropoly Acid (Component B) | Ratio A:B (wt) | Conv (%) | 16HD | THPM | 12HD | 12CHD* | 1H |
|---|---|---|---|---|---|---|---|---|---|---|
| 16 | 220 | CuO/SiO$_2$ (i)         | Cs$_{2.5}$H$_{0.5}$PW$_{12}$O$_{40}$ | 1:1 | 9   | 4  | 5  | <1 | 1  | <1 |
| 17 | 220 | CuO/MnO$_2$/Al$_2$O$_3$ | Cs$_{2.5}$H$_{0.5}$PW$_{12}$O$_{40}$ | 1:1 | 18  | 2  | 5  | <1 | 2  | <1 |
| 18 | 220 | CuO/Cr$_2$O$_3$/MnO$_2$ | Cs$_{2.5}$H$_{0.5}$PW$_{12}$O$_{40}$ | 1:1 | 98  | 4  | 23 | 1  | 15 | <1 |
| 19 | 220 | BaO/CuO/Cr$_2$O$_3$     | Cs$_{2.5}$H$_{0.5}$PW$_{12}$O$_{40}$ | 1:1 | 8   | <1 | 2  | <1 | 1  | <1 |
| 20 | 220 | CuO/SiO$_2$ (ii)        | Cs$_{2.5}$H$_{0.5}$PW$_{12}$O$_{40}$ | 1:1 | 89  | 19 | 24 | 1  | 4  | <1 |
| 21 | 220 | CuO/Cr$_2$O$_3$         | Cs$_{2.5}$H$_{0.5}$PW$_{12}$O$_{40}$ | 1:1 | 76  | 5  | 25 | 1  | 15 | <1 |
| 22 | 220 | CuO/ZnO/Al$_2$O$_3$     | Cs$_{2.5}$H$_{0.5}$PW$_{12}$O$_{40}$ | 1:1 | 12  | <1 | 7  | <1 | 5  | <1 |
| 23 | 250 | CuO/SiO$_2$ (i)         | Cs$_{2.5}$H$_{0.5}$PW$_{12}$O$_{40}$ | 1:1 | 6   | 1  | 5  | 1  | <1 | 1  |
| 24 | 250 | CuO/MnO$_2$/Al$_2$O$_3$ | Cs$_{2.5}$H$_{0.5}$PW$_{12}$O$_{40}$ | 1:1 | 47  | <1 | 17 | 9  | <1 | 1  |
| 25 | 250 | CuO/Cr$_2$O$_3$/MnO$_2$ | Cs$_{2.5}$H$_{0.5}$PW$_{12}$O$_{40}$ | 1:1 | 94  | 9  | 24 | 17 | <1 | 1  |
| 26 | 250 | BaO/CuO/Cr$_2$O$_3$     | Cs$_{2.5}$H$_{0.5}$PW$_{12}$O$_{40}$ | 1:1 | 47  | 1  | 9  | 9  | <1 | 1  |
| 27 | 250 | CuO/SiO$_2$ (ii)        | Cs$_{2.5}$H$_{0.5}$PW$_{12}$O$_{40}$ | 1:1 | 100 | 29 | 24 | 3  | <1 | 1  |
| 28 | 250 | CuO/Cr$_2$O$_3$         | Cs$_{2.5}$H$_{0.5}$PW$_{12}$O$_{40}$ | 1:1 | 100 | 9  | 22 | 12 | <1 | 1  |

*12CHD yield reported as the sum of cis- and trans- isomers
(i) CuO/SiO$_2$ obtained from BASF
(ii) CuO/SiO2 obtained from Evonik

TABLE 4

Hydrodeoxygenation Results for Comparative Examples

| Comp Ex | Temp (°C.) | First Metal Component (Component A) | Heteropoly Acid (Component B) | Conv (%) | 16HD | THPM | 12HD | 15HD | 12CHD* | 1H |
|---|---|---|---|---|---|---|---|---|---|---|
| A | 260 | CuO/MnO$_2$/Al$_2$O$_3$ | None                                 | 18  | 1  | 6  | <1 | <1 | <1 | <1 |
| B | 250 | CuO/ZnO                 | None                                 | 46  | 2  | 23 | <1 | 2  | <1 | 1  |
| C | 250 | CuO/SiO$_2$ (i)         | None                                 | 23  | 4  | 13 | <1 | <1 | 3  | <1 |
| D | 220 | CuO/SiO$_2$ (ii)        | None                                 | 12  | <1 | 5  | <1 | <1 | <1 | <1 |
| E | 220 | CuO/ZnO                 | None                                 | 5   | <1 | 5  | <1 | <1 | <1 | <1 |
| F | 220 | none                    | Cs$_{2.5}$H$_{0.5}$PW$_{12}$O$_{40}$ | 100 | <1 | <1 | <1 | <1 | <1 | <1 |
| G | 260 | none                    | Cs$_{2.5}$H$_{0.5}$PW$_{12}$O$_{40}$ | 100 | <1 | <1 | <1 | <1 | <1 | <1 |
| H | 260 | none                    | H$_3$PW$_{12}$O$_{40}$               | 100 | <1 | <1 | <1 | <1 | <1 | <1 |

*12CHD yield reported as the sum of cis- and trans- isomers

The results for Comparative Examples A-H show that using CuO/MnO$_2$/Al$_2$O$_3$ (Comp Ex A) or CuO/Zn (Comp Ex B) or CuO/SiO$_2$ (Comp Ex C and D) or CuO/ZnO (Comp Ex E) catalysts without a heteropoly acid component, or a heteropoly acid component without a first metal component (Comp Ex F, G, and H), resulted in no or little formation of 16HD from 126HT.

Example 29

Conversion of 126HT to a Product Mixture Comprising 16HD and THPM Using a Cu/SiO$_2$/H$_3$PW$_{12}$O$_{40}$ Catalyst (16 h)

To a stainless steel (SS316) pressure reactor equipped with a magnetic stir bar and 9.5 mL of water were added about 500 mg of 1,2,6-hexanetriol and about 800 mg of Cu/SiO$_2$/H$_3$PW$_{12}$O$_{40}$ catalyst (1:1 Cu/SiO$_2$: H$_3$PW$_{12}$O$_{40}$ by weight) prepared using Method A. The reactor was sealed, connected to a high pressure gas manifold, and purged with nitrogen gas (1000 psi, 6895 kPa) three times. About 500 psi (3447 kPa) of hydrogen was then added, the reactor was heated to 260° C. and the pressure was adjusted to 1000 psi (6895 kPa). After 16 h, the reactor was allowed to cool to room temperature within 2 h and depressurized. The reaction product solution was diluted with n-propanol and a known amount of diethylene glycol diethyl ether as an internal standard and filtered through a standard 5 micron disposable filter. A sample was taken and analyzed by GC and GC/MS; results are given in Table 5.

Example 30

This Example was carried out as described in Example 29 but the reaction was stopped after 4 h. Results are given in Table 5.

TABLE 5

Results for Examples 29 and 30

| Ex | Reaction time [h] | 16HD Molar Yield (%) | THPM Molar Yield (%) | 1,2HD Molar Yield (%) | 1,2-CHD Molar Yield (%) | Other Diols Molar Yield (%) | Conv (%) |
|---|---|---|---|---|---|---|---|
| 29 | 16 | 71 | 23 | 8 | 1 | <1 | 94 |
| 30 | 4 | 21 | 49 | 3 | <1 | 1 | 82 |

The results in Table 5 indicate that under the reaction conditions used, the catalyst promoted the conversion of 126HT to THPM and 16HD, and the conversion of THPM to 16HD.

Catalyst Preparation Method C

Preparation of CuW/Cs$_{2.5}$H$_{0.5}$P W$_3$O$_{10}$)$_4$ Catalyst 4% Cu; W/Cu=1)

0.48 g of Cs$_{2.5}$H$_{0.5}$P(W$_3$O$_{10}$)$_4$ (prepared as described herein above) that had been ground with a mortar and pestle and passed through a 400 microns mesh sieve was impregnated with 0.076 g of copper(II) nitrate hydrate dissolved in 0.5 mL of water. The resulting slurry was mixed for 15 minutes, then dried overnight in a vacuum oven at 110° C. The resulting solid was allowed to cool to room temperature, and then wetted again with 0.5 mL of water. To this was added 0.082 g of ammonium tungsten oxide hydrate dissolved in 2.0 mL of water. The resulting mixture was stirred for 15 minutes. The vial was then placed into a vacuum oven and its contents dried overnight at 110° C. After cooling to room temperature, the material was transferred to a ceramic boat and calcined in air at 350° C. for three hours.

CuW/Cs$_{2.5}$H$_{0.5}$P(W$_3$O$_{10}$)$_4$ catalyst containing 10% Cu and having W/Cu=1 was prepared according to the above procedure except that 0.190 g of copper(II) nitrate hydrate and 0.205 g of ammonium tungsten oxide hydrate were used.

The catalysts prepared according to Method C were used in Examples 31-36. Results are presented in Table 6.

Catalyst Preparation Method D

Preparation of Cu/Cs$_{2.5}$H$_{0.5}$P(W$_3$O$_{10}$)$_4$ Catalyst Containing 4 Wt % Cu 0.48 g of Cs$_{2.5}$H$_{0.5}$P(W$_3$O$_{10}$)$_4$ (prepared as described herein above) that had been ground with a mortar and pestle and passed through a 400 microns mesh sieve was impregnated with 0.076 g of copper(II) nitrate hydrate dissolved in 0.5 mL of water. The resulting slurry was mixed for 15 minutes, then dried overnight in a vacuum oven at 110° C. After cooling to room temperature, the material was transferred to a ceramic boat and calcined in air at 350° C. for three hours.

Cu/Cs$_{2.5}$H$_{0.5}$P(W$_3$O$_{10}$)$_4$ catalysts containing 10 wt % Cu or 20 wt % Cu were prepared according to the above procedure except that 0.190 g or 0.380 g of copper(II) nitrate hydrate were used, respectively.

The catalysts prepared according to Method D were used in Examples 37-39. Results are presented in Table 6.

Catalyst Preparation Method E

Preparation of 4% Cu/15% Cs$_{2.5}$H$_{0.5}$P(W$_3$O$_{10}$)$_4$ on SiO$_2$ Catalyst 0.48 g of 15% Cs$_{2.5}$H$_{0.5}$P(W$_3$O$_{10}$)$_4$ on SiO$_2$ (prepared as described herein above) that had been ground with a mortar and pestle and passed through a 400 microns mesh sieve was impregnated with 0.076 g of copper(II) nitrate hydrate dissolved in 0.5 mL of water. The resulting slurry was mixed for 15 minutes, then dried overnight in a vacuum oven at 110° C. After cooling to room temperature, the material was transferred to a ceramic boat and calcined in air at 350° C. for three hours.

This catalyst was used in Example 40. Results are presented in Table 6.

Examples 31-40

Hydrodeoxygenation of 1,2,6-Hexanetriol

In Examples 31-40, catalysts prepared according to Method C, D, or E were used to convert 126HT to a product mixture comprising 16HD according to the following procedure. The catalysts were used without pre-reduction.

Conversion of 1,2,6-hexanetriol to a reaction mixture comprising 1,6-hexanediol was performed by placing approximately 1 g of an aqueous solution of 126HT (5 weight percent) and approximately 50 mg of the catalyst indicated in Table 6 with a stir bar into a 1.5 mL pressure vessel. The vessel was charged with H$_2$ to the reaction pressure vessel shown in Table 6, then heated to the reaction temperature shown. The designated pressure (1000 psig) and temperature were maintained for 4 hours, the vessel then cooled to room temperature, the reaction mixture filtered, and the reaction solution analyzed using GC methods calibrated with internal standards. Results are presented in Table 6.

TABLE 6

Hydrodeoxygenation Results for Catalysts made by Catalyst Preparation Method C, D, or E

| Ex | Temp (°C.) | Catalyst | M1 | M1 wt % | M2 | M2/M1 Molar ratio | Conversion (%) | Yield (%) 16HD | THPM | 12HD | 1H |
|---|---|---|---|---|---|---|---|---|---|---|---|
| 31 | 250 | CuW/Cs$_{2.5}$H$_{0.5}$P(W$_3$O$_{10}$)$_4$ | Cu | 4 | W | 1 | 100 | 4.8 | 8.5 | 4.5 | 0.8 |
| 32 | 250 | CuW/Cs$_{2.5}$H$_{0.5}$P(W$_3$O$_{10}$)$_4$ | Cu | 10 | W | 1 | 100 | 6.8 | 10.2 | 3.5 | 1.0 |
| 33 | 200 | CuW/Cs$_{2.5}$H$_{0.5}$P(W$_3$O$_{10}$)$_4$ | Cu | 4 | W | 1 | 86.1 | 26.2 | 34.8 | 4.5 | 0.4 |
| 34 | 200 | CuW/Cs$_{2.5}$H$_{0.5}$P(W$_3$O$_{10}$)$_4$ | Cu | 10 | W | 1 | 82.4 | 21.9 | 30.6 | 3.2 | 0.5 |
| 35 | 220 | CuW/Cs$_{2.5}$H$_{0.5}$P(W$_3$O$_{10}$)$_4$ | Cu | 4 | W | 1 | 100 | 26.4 | 27.5 | 1.7 | 0.9 |
| 36 | 220 | CuW/Cs$_{2.5}$H$_{0.5}$P(W$_3$O$_{10}$)$_4$ | Cu | 10 | W | 1 | 100 | 20.7 | 28.9 | 5.0 | 1.0 |
| 37 | 250 | Cu/Cs$_{2.5}$H$_{0.5}$P(W$_3$O$_{10}$)$_4$ | Cu | 10 | — | — | 100 | 5.1 | 9.7 | 3.8 | 0.2 |
| 38 | 250 | Cu/Cs$_{2.5}$H$_{0.5}$P(W$_3$O$_{10}$)$_4$ | Cu | 20 | — | — | 100 | 24.6 | 18.5 | 1.8 | 1.6 |
| 40 | 250 | Cu/15% Cs$_{2.5}$H$_{0.5}$P(W$_3$O$_{10}$)$_4$ on SiO$_2$ | Cu | — | — | — | 65.1 | 13.0 | 15.9 | 0.5 | 1.0 |

What is claimed is:

1. A process for preparing an α,ω-C$_n$-diol, comprising the steps:
    (a) providing a feedstock comprising a C$_n$ oxygenate;
    (b) contacting the feedstock with hydrogen gas, in the presence of a catalyst and at a temperature and for a time sufficient to form a product mixture comprising an α,ω-C$_n$-diol;
    wherein n is 5 or greater; and wherein the catalyst comprises a first metal component, a heteropoly acid component, optionally a second metal component, optionally at least one promoter, and optionally a support; wherein:
    the first metal component comprises Cu, a Cu oxide, or mixtures thereof;
    the heteropoly acid component comprises H$_3$[P(W$_3$O$_{10}$)$_4$], H$_4$[Si(W$_3$O$_{10}$)$_4$], H$_4$[P(Mo$_3$O$_{10}$)$_4$], H$_4$[Si(Mo$_3$O$_{10}$)$_4$], Cs$_{2.5}$H$_{0.5}$[P(W$_3$O$_{10}$)$_4$], Cs$_{2.5}$H$_{0.5}$[Si(W$_3$O$_{10}$)$_4$], or mixtures thereof;
    the second metal component comprises Cr, a Cr oxide, Ni, a Ni oxide, Mn, a Mn oxide, Fe, an Fe oxide, Co, a Co oxide, Mo, a Mo oxide, W, a W oxide, Re, a Re oxide, Zn, or a Zn oxide, Ag, a Ag oxide, SiO$_2$, or Al$_2$O$_3$; and
    the promoter comprises Na, K, Mg, Rb, Cs, Ca, Sr, Ba, Ce, or mixtures thereof.

2. The process of claim 1 wherein n=5 or 6.

3. The process of claim 1, wherein the optional support is present in the catalyst and comprises WO$_3$, SiO$_2$, Al$_2$O$_3$, carbon, TiO$_2$, ZrO$_2$, SiO$_2$—Al$_2$O$_3$, montmorillonite, SiO$_2$—TiO$_2$, tungstated ZrO$_2$, zeolites, V$_2$O$_5$, MoO$_3$, or mixtures thereof.

4. The process of claim 3, wherein the support comprises SiO$_2$.

5. The process of claim 1, wherein the C$_n$ oxygenate comprises 1,2,6-hexanetriol; 1,2,5-pentanetriol; 2H-tetrahydropyran-2-methanol; tetrahydrofuran-2,5-dimethanol; furan-2,5-dimethanol; 2,5 dihydrofuran-2,5-dimethanol; levoglucosenone; levoglucosan; isosorbide; hydroxymethylfurfural; sorbitol; glucose; fructose; xylitol; 3,4-dihydro-2H-pyran-2-carbaldehyde; 1,2,5,6-hexanetetraol; 1,2,3,5,6-hexanepentanol; 1,5-anhydro-3,4-dideoxy-hexitol; 5-hydroxy-2H-tetrahydropyran-2 methanol; furfural; furfuryl alcohol; tetrahydrofurfuryl alcohol; pentoses; dimers containing pentose; oligomers containing pentose; hexoses; dimers containing hexose; oligomers containing hexose; condensation products from the reaction of 5-(hydroxymethyl)-2-furfural with ketones and/or aldehydes; and condensation products from the reaction of furfural with ketones and/or aldehydes.

6. The process of claim 5, wherein the C$_n$ oxygenate comprises 1,2,6-hexanetriol; 2H-tetrahydropyran-2-methanol; tetrahydrofuran-2,5-dimethanol; levoglucosenone; 3,4-dihydro-2H-pyran-2-carbaldehyde, or mixtures thereof.

7. The process of claim 6, wherein the C$_n$ oxygenate comprises 1,2,6-hexanetriol.

8. The process of claim 5, wherein the C$_n$ oxygenate comprises 1,2,5-pentanetriol; furfural; furfuryl alcohol; tetrahydrofurfuryl alcohol; xylitol; or mixtures thereof.

9. The process of claim 1, wherein the heteropoly acid component comprises H$_3$[P(W$_3$O$_{10}$)$_4$], H$_4$[Si(W$_3$O$_{10}$)$_4$], or Cs$_{2.5}$H$_{0.5}$[P(W$_3$O$_{10}$)$_4$].

10. The process of claim 1, wherein the optional second metal component is present in the catalyst and comprises Cr, a Cr oxide, Mn, a Mn oxide, Zn, a Zn oxide, or mixtures thereof.

11. The process of claim 1, wherein the optional promoter is present in the catalyst and comprises Ba, Cs, or mixtures thereof.

12. The process of claim 1, wherein the catalyst comprises from 2 weight percent to 98 weight percent Cu and/or CuO, and further comprises from 98 weight percent to 2 weight percent of at least one oxide selected from the group consisting of zinc oxide, magnesium oxide, barium oxide, chromium oxide, silica, alumina, zirconium dioxide, nickel oxide, manganese oxide, sodium oxide, potassium oxide, cerium oxide, lanthanum oxide, iron oxide, silver oxide, and cobalt oxide, based on the total weight of the first metal component and the second metal component.

13. The process of claim 1, further comprising the steps:
    (c) optionally, isolating the α,ω-C$_n$-diol from the product mixture;
    (d) contacting the α,ω-C$_n$-diol with ammonia and hydrogen in the presence of a reductive amination catalyst at a temperature and for a time sufficient to form a second product mixture comprising an α,ω-C$_n$-diaminoalkane; and
    (e) optionally, isolating the α,ω-C$_n$-diaminoalkane from the second product mixture.

14. The process of claim 13, wherein the α,ω-C$_n$-diaminoalkane comprises 1,6-diaminohexane.

* * * * *